(12) United States Patent
Jorgensen

(10) Patent No.: US 9,962,168 B2
(45) Date of Patent: May 8, 2018

(54) METHOD AND APPARATUS FOR PERFORMING MINIMALLY INVASIVE ARTHROSCOPIC PROCEDURES

(71) Applicant: CroJor, LLC, Ponte Vedra Beach, FL (US)

(72) Inventor: Glen Jorgensen, Jacksonville, FL (US)

(73) Assignee: CROJOR, LLC, Ponte Vedra Beach, FL (US)

( * ) Notice: Subject to any disclaimer, the term of this patent is extended or adjusted under 35 U.S.C. 154(b) by 714 days.

(21) Appl. No.: 14/534,757

(22) Filed: Nov. 6, 2014

(65) Prior Publication Data

US 2015/0066033 A1    Mar. 5, 2015

Related U.S. Application Data

(63) Continuation-in-part of application No. 14/224,897, filed on Mar. 25, 2014, which is a continuation of
(Continued)

(51) Int. Cl.
*A61B 17/16* (2006.01)
*A61B 17/32* (2006.01)
(Continued)

(52) U.S. Cl.
CPC ........ *A61B 17/1615* (2013.01); *A61B 1/0055* (2013.01); *A61B 1/00087* (2013.01); *A61B 1/05* (2013.01); *A61B 1/317* (2013.01); *A61B 17/1671* (2013.01); *A61B 17/32002* (2013.01); *A61B 17/320016* (2013.01); *A61B 34/71* (2016.02); *A61B 1/00165* (2013.01); *A61B 18/1482* (2013.01); *A61B 34/70* (2016.02); *A61B 2017/003* (2013.01); *A61B 2017/00314* (2013.01); *A61B 2017/00867* (2013.01); *A61B 2017/2929* (2013.01);
(Continued)

(58) Field of Classification Search
CPC ............ A61B 17/1615; A61B 17/1617; A61B 17/1637; A61B 17/1642; A61B 17/1659–17/1671; A61B 17/1684; A61B 17/16; A61B 17/32002
USPC .......................................................... 606/1
See application file for complete search history.

(56) References Cited

U.S. PATENT DOCUMENTS

| 4,669,467 A | 6/1987 | Willett et al. |
| 5,306,245 A | 4/1994 | Heaven |

(Continued)

FOREIGN PATENT DOCUMENTS

| EP | 1586275 A2 | 10/2005 |
| WO | 2005/086839 | 9/2005 |

OTHER PUBLICATIONS

Supplemental European Search Report for EP 06848010.2, dated Jan. 14, 2010, 3 pp.

*Primary Examiner* — Matthew Lawson
*Assistant Examiner* — Amy Sipp
(74) *Attorney, Agent, or Firm* — James A. Sheridan; Sheridan Law, LLC

(57) ABSTRACT

A surgical device capable of interconnecting to an external motorized hand pieces, bending a distal end segment, rotating a window element positioned distal to the distal end segment and rotating independently of it, and actuating a cutting element positioned within the outer window element and rotating independently of it.

19 Claims, 16 Drawing Sheets

Related U.S. Application Data application No. 12/399,471, filed on Mar. 6, 2009, now Pat. No. 8,679,097, which is a continuation-in-part of application No. 12/119,799, filed on May 13, 2008, which is a continuation of application No. 11/643,740, filed on Dec. 20, 2006.

(60) Provisional application No. 60/752,284, filed on Dec. 20, 2005.

(51) Int. Cl.
   *A61B 1/005* (2006.01)
   *A61B 1/05* (2006.01)
   *A61B 1/317* (2006.01)
   *A61B 1/00* (2006.01)
   *A61B 18/14* (2006.01)
   *A61B 17/00* (2006.01)
   *A61B 17/29* (2006.01)
   *A61B 18/00* (2006.01)
   *A61B 34/00* (2016.01)

(52) U.S. Cl.
   CPC ........... *A61B 2017/2948* (2013.01); *A61B 2018/00595* (2013.01); *A61B 2018/00607* (2013.01); *A61B 2018/00982* (2013.01)

(56) References Cited

U.S. PATENT DOCUMENTS

| | | |
|---|---|---|
| 5,318,528 A | 6/1994 | Heaven et al. |
| 5,322,505 A | 6/1994 | Krause et al. |
| 5,411,514 A | 5/1995 | Fucci et al. |
| 5,439,478 A | 8/1995 | Palmer |
| 5,454,827 A | 10/1995 | Aust et al. |
| 5,507,297 A | 4/1996 | Slater et al. |
| 5,510,070 A | 4/1996 | Krause et al. |
| 5,601,591 A | 2/1997 | Edwards et al. |
| 5,618,293 A | 4/1997 | Sample et al. |
| 5,618,294 A | 4/1997 | Aust et al. |
| 5,643,294 A | 7/1997 | Tovey et al. |
| 5,643,303 A | 7/1997 | Donahue |
| 5,766,196 A | 6/1998 | Griffiths |
| 5,782,834 A | 7/1998 | Lucey et al. |
| 5,797,959 A | 8/1998 | Castro et al. |
| 5,810,828 A * | 9/1998 | Lightman ............ A61B 17/164 606/80 |
| 5,836,960 A | 11/1998 | Kolesa et al. |
| 5,899,914 A | 5/1999 | Zirps et al. |
| 5,938,678 A | 8/1999 | Zirps et al. |
| 6,193,715 B1 * | 2/2001 | Wrublewski ....... A61B 18/1402 604/22 |
| 6,228,023 B1 | 5/2001 | Zaslavsky et al. |
| 6,352,503 B1 | 3/2002 | Matsui et al. |
| 6,423,059 B1 | 7/2002 | Hanson et al. |
| 6,464,711 B1 | 10/2002 | Emans et al. |
| 6,500,189 B1 | 12/2002 | Lang et al. |
| 6,533,749 B1 | 3/2003 | Mitusina et al. |
| 6,569,105 B1 | 5/2003 | Kortenbach et al. |
| 6,645,218 B1 * | 11/2003 | Cassidy ............ A61B 17/32002 606/170 |
| 6,656,195 B2 | 12/2003 | Peters et al. |
| 6,695,772 B1 | 2/2004 | Bon et al. |
| 6,743,239 B1 | 6/2004 | Kuehn et al. |
| 7,033,357 B2 | 4/2006 | Baxter et al. |
| 7,090,637 B2 | 8/2006 | Danitz et al. |
| 7,090,683 B2 | 8/2006 | Brock et al. |
| 7,147,650 B2 | 12/2006 | Lee |
| 7,169,141 B2 | 1/2007 | Brock et al. |
| 7,214,230 B2 | 5/2007 | Brock et al. |
| 7,229,456 B2 | 6/2007 | Lang et al. |
| 7,303,560 B2 | 12/2007 | Chin et al. |
| 7,338,513 B2 | 3/2008 | Lee et al. |
| 7,364,582 B2 | 4/2008 | Lee |
| 7,371,210 B2 | 5/2008 | Brock et al. |
| 7,585,300 B2 | 9/2009 | Cha |
| 2003/0135204 A1 | 7/2003 | Lee et al. |
| 2004/0102772 A1 | 5/2004 | Baxter et al. |
| 2004/0138525 A1 | 7/2004 | Saadat et al. |
| 2005/0043682 A1 | 2/2005 | Kucklick et al. |
| 2005/0096694 A1 * | 5/2005 | Lee .................. A61B 17/00234 606/205 |
| 2005/0119527 A1 | 6/2005 | Banik et al. |
| 2005/0159765 A1 | 7/2005 | Moutafis et al. |
| 2005/0187543 A1 | 8/2005 | Underwood et al. |
| 2005/0197623 A1 | 9/2005 | Leeflang et al. |
| 2005/0209622 A1 | 9/2005 | Carrison |
| 2005/0216033 A1 | 9/2005 | Lee et al. |
| 2006/0095074 A1 | 5/2006 | Lee et al. |

* cited by examiner

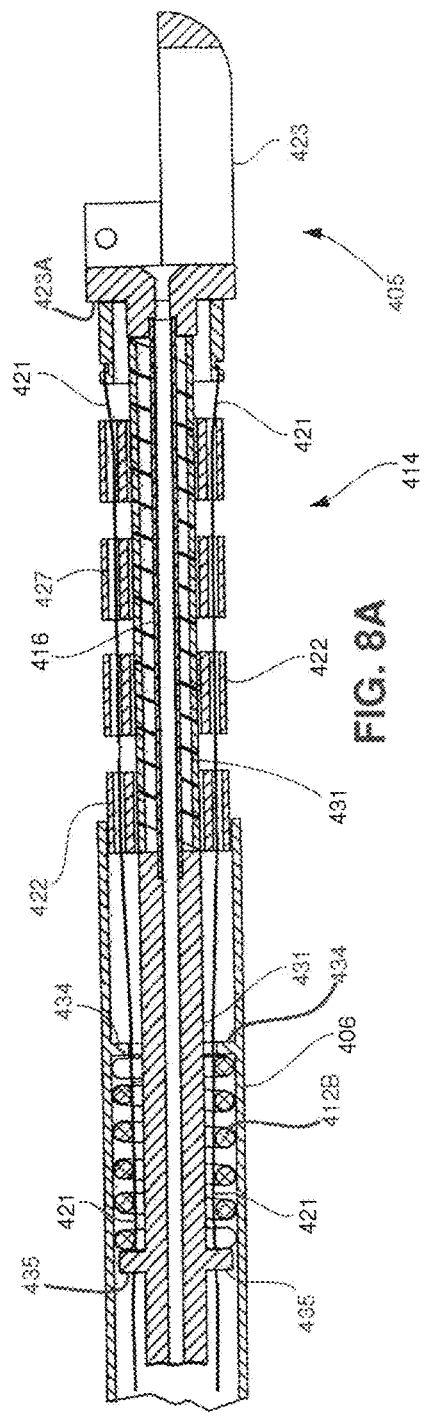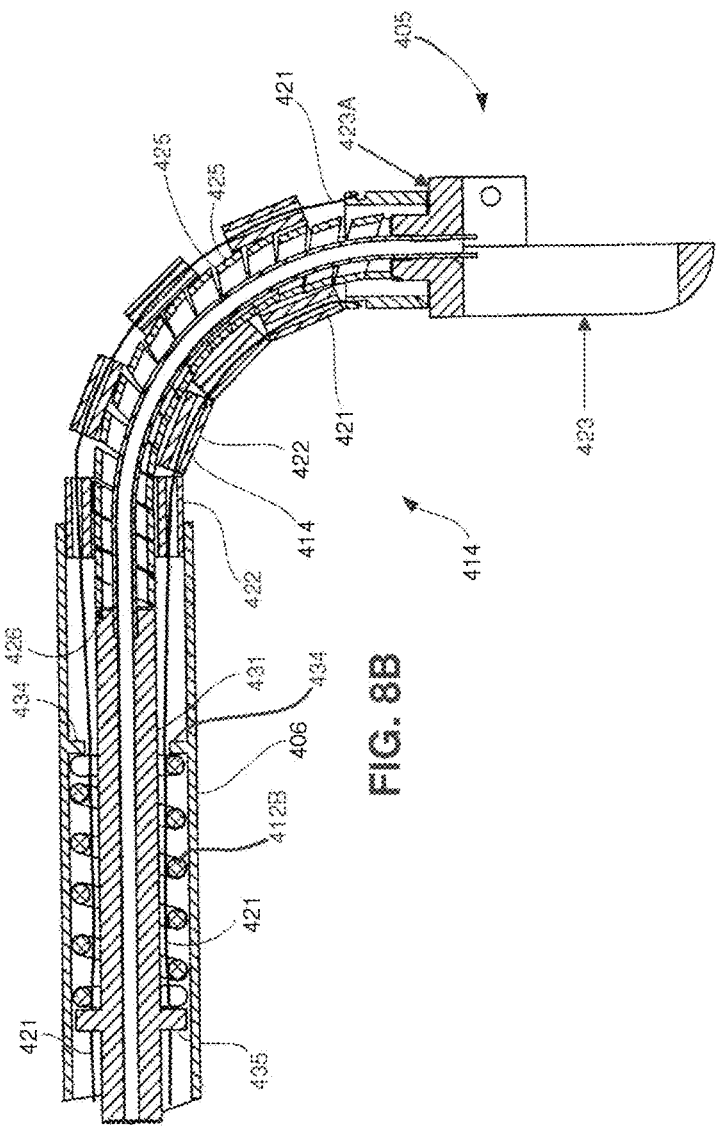

METHOD AND APPARATUS FOR PERFORMING MINIMALLY INVASIVE ARTHROSCOPIC PROCEDURES

REFERENCE TO PENDING PRIOR PATENT APPLICATIONS

This patent application is a continuation-in-part of pending prior U.S. patent application Ser. No. 14/224,897, filed Mar. 25, 2014 by Glen Jorgensen et al. for METHOD AND DEVICES FOR MINIMALLY INVASIVE ARTHROSCOPIC PROCEDURES, which patent application is a continuation of prior U.S. patent application Ser. No. 12/399,471, filed Mar. 6, 2009 by Glen Jorgensen et al. for METHOD AND DEVICES FOR MINIMALLY INVASIVE ARTHROSCOPIC PROCEDURES, which is a continuation-in-part of prior U.S. patent application Ser. No. 12/119,799, filed May 13, 2008 by Glen Jorgensen for METHOD AND DEVICES FOR MINIMALLY INVASIVE ARTHROSCOPIC PROCEDURES, which is a continuation of prior U.S. patent application Ser. No. 11/643,740, filed Dec. 20, 2006 by Glen Jorgensen for METHOD AND DEVICES FOR MINIMALLY INVASIVE ARTHROSCOPIC PROCEDURES, which claims benefit of prior U.S. Provisional Patent Application Ser. No. 60/752,284, filed Dec. 20, 2005 by Glen Jorgensen for METHOD AND DEVICES FOR MINIMALLY INVASIVE ARTHROSCOPIC PROCEDURES.

The five (5) above-identified patent applications are hereby incorporated herein by reference.

FIELD OF THE INVENTION

This invention relates to surgical methods and apparatus in general, and more particularly to methods and apparatus for performing arthroscopic procedures, particularly arthroscopic procedures on the hip, including arthroscopic diagnostic and surgical procedures.

BACKGROUND OF THE INVENTION

Access to the knee and/or shoulder joints during arthroscopic surgery is typically made through two portals, often referred to as the operative portal and the visualization portal. An arthroscope is inserted through the visualization portal, while a surgical instrument is inserted through the operative portal. If desired, the role of the visualization portal can be interchanged with the role of the operative portal to provide better viewing of, and/or better access to, internal capsular structures.

The hip is complex and difficult to access using arthroscopic techniques. FIGS. 1, 2A, 2B, 2C and 2D illustrate the basic anatomy of the hip. For the sake of simplification, FIGS. 1, 2A, 2B, 2C and 2D do not show the surrounding synovial membrane, the femoral ligament complex, the adductor muscle structure, varying layers of fat, and other tissue, all of which compound the difficulty in accessing the joint capsule. There are also many delicate structures surrounding the hip joint that are not shown in FIGS. 1, 2A, 2B, 2C and 2D, e.g., the anterior femoral neurovascular bundle, the lateral femoral cutaneous nerve, the lateral femoral circumflex artery and the sciatic nerve, among others. Damage to these structures can be permanent and irreparable, so care must be taken to avoid harming these structures during surgery.

Typically, access to the hip joint for minimally invasive arthroscopic surgery is achieved through two access cannulas which line the aforementioned operative portal and visualization portal. The two access cannulas are typically positioned in the so-called posterolateral and anterolateral positions, which are located 1-2 cm above (superior) and 1-2 cm on each side of the landmark greater trocanter (see FIG. 3). Typically, the arthroscope is disposed in the posterolateral position and the surgical instrument (e.g., forceps, dissector, scissors, scalpel, punch, probe, powered shaver, manual graspers, electrocautery wand, etc.) is disposed in the anterolateral position. However, as noted above, it is common to interchange this positioning in order to improve visualization and/or access to the target site.

Despite the ability to interchange the positioning of the arthroscope and surgical instrument, areas of the distended surfaces of the hip joint are generally not able to be fully visualized. FIG. 3 shows one such "No See" zone. The regions of the hip joint which are not accessible by straight and rigid surgical instruments is even larger due to the anatomy of the hip joint and the fixed geometry of the surgical instruments. For example, if the target site is in a region that is located on the far side of the femoral head, a third portal must often be established in the so-called anterior position. However, this anterior portal considerably increases the risk associated with the procedure, due to the proximity of the third portal to the lateral femoral cutaneous nerve, the lateral femoral circumflex artery and the femoral neurovascular bundle. Unfortunately, access via the opposite, posterior side of the joint, i.e., via the gluteal region, is generally not a viable option, nor is access via a medial approach from the groin.

Roughly half of the distended hip joint is inaccessible via the normal, accepted portal placement positions (i.e., the aforementioned posterolateral and anterolateral positions). While visualization can be improved somewhat by physically "prying" the access cannulas into a contrived position, and/or by performing excessive capsulectomies, access remains a significant hurdle to the performance of arthroscopic procedures on the hip.

The preferred solution would be to provide steerable surgical instruments that can enter the capsule of the hip joint in a straight configuration through any of the access portals commonly used (e.g., the aforementioned posterolateral and anterolateral portals), and then be steered into a "No See" zone, e.g., as depicted in FIG. 4. Preferably, this steerable surgical instrument would have a robust straight section 120 and a steerable section 122 that is set to a straight configuration during insertion into the capsule and is then steered into the operable position through the manipulation of controls housed in an instrument handle positioned outside the capsule and connected to the proximal end of straight section 122.

SUMMARY OF THE INVENTION

This invention generally relates to methods and apparatus for performing arthroscopic procedures, particularly arthroscopic procedures on the hip. The methods and apparatus of the present invention provide access to regions of the spherically-shaped hip joint that are inaccessible using current arthroscopic instrumentation.

The methods and apparatus of the present invention can be suitably used to perform arthroscopic procedures not only on the hip joint, but also on other parts of the anatomy that require flexible access, e.g., the knee joint, the shoulder joint, etc. The methods and apparatus of the present invention are not limited to arthroscopy, and can further be used in endoscopic and laparoscopic procedures as well as in open surgical procedures.

One form of the present invention generally relates to the provision and use of a surgical instrument for diagnostic or surgical procedures, wherein the surgical instrument comprises:

a handle disposed at the proximal end of the surgical instrument;

an elongate outer tube having a proximal end and a distal end, the elongate outer tube extending distally from the handle;

a flexible, distal end segment extending from the distal end of the elongate outer tube;

an operable tip comprising an outer cutting window member and an inner cutting member;

the outer cutting window member of the operable tip being rotatably mounted to the distal end of an inner extension tube, the inner extension tube having its proximal end connected to a rotation control knob in the handle;

an actuation means for rotating the inner cutting member of the operable tip via a flexible actuating cable or a high-speed inner extension tube;

manipulation mechanisms at the proximal end of the surgical instrument for manipulating the disposition of the flexible distal end segment;

wherein the surgical instrument provides at least the following independent degrees of freedom: curvilinear bending of the flexible distal end segment to provide the flexible distal end segment with an arcuate axis, rotation of the outer cutting window member of the operable tip about the arcuate axis of the flexible distal end segment, and rotation of the inner cutting member of the operable tip relative to the outer cutting window member of the operable tip.

In another form of the present invention, the invention generally comprises the provision and use of a surgical instrument for performing diagnostic and/or surgical procedures, the surgical instrument comprising:

a handle at the proximal end of the surgical instrument;

an operable tip rotatably mounted at the distal end of the surgical instrument, the operable tip comprising an outer cutting window member and an inner cutting member;

a rigid elongated outer tube fixed relative to the handle and interconnected with a flexible distal end segment;

the outer cutting window member of the operable tip connected to an inner extension tube;

a spring preloading means to bias the outer cutting window member into contact with the flexible distal end segment;

a rotation control knob in the handle connected to the inner extension tube;

the inner cutting member of the operable tip, preferably a high speed cutting element, being rotatably mounted at the distal end of a flexible actuating cable or a high-speed inner extension tube;

flexion control means for bending the flexible distal end segment, the flexion control means comprising a bending cam and one or more pairs of tensioning members interconnecting the bending cam and the flexible distal end segment, wherein manipulation of the bending cam places a tensile force on one or more tensioning members and causes the flexible distal end segment to bend proportionally to the tensile force, and wherein bending of the flexible distal end segment provides the flexible distal end segment with an arcuate axis;

a rotation control knob in connection with the operable tip for rotating the outer cutting window member of the operative tip about the arcuate axis of the flexible distal end segment; and an external drive mechanism in flexible connection with the inner cutting member of the operable tip, preferably a high-speed cutting element.

In another form of the invention, the outer cutting window member of the operable tip is held in place relative to the flexible distal end segment by the tensioning members in a manner that secures the outer cutting window member relative to the flexible distal end segment and in a manner that allows the outer cutting window member to be rotated before insertion into the joint by gripping the outer cutting window member directly and rotating it by hand to a desired position.

Embodiments according to these aspects of the invention can include the following features.

The surgical instrument can be designed for use in medical procedures performed on the hip (e.g., arthroscopic procedures on the hip) and the flexible tensioning members, the inner extension tube and the flexible distal end segment can take on a curved profile having a bend radius corresponding to the curvature of the femoral head. In some embodiments of the present invention, the bend radius can be approximately 25 mm. It should also be appreciated that the present invention can also be designed for use in medical procedures on the knee or shoulder, and the bend radius can be less than 25 mm. In some embodiments of the present invention, the bend radius can be approximately 12 mm. The device can be configured for use in medical procedures on the elbow, wrist, or intraverterbral spaces, and the bend radius can be less than 12 mm. In some embodiments, the bend radius can range from about 1 mm to about 5 mm. The surgical instrument can be for use in general abdominal laparoscopy, and the bend radius can range from about 25 mm to about 50 mm.

The flexible tensioning members, the inner extension tube and the flexible distal end segment preferably have a cylindrical shape with a circular cross-section. These elements can comprise a lightweight and strong bio-compatible material. By way of example but not limitation, the material may comprise surgical grade stainless steel, anodized aluminum, polymeric materials or composites. The materials of the flexible distal end segment can be chosen so as to provide excellent lubricious bearing properties for the support of a high-speed rotating inner extension tube.

The operable end of the surgical instrument can comprise cylindrical elements rotationally movable relative to each other, and the surgical instrument can further include actuation or control mechanisms at its proximal end.

A first actuation mechanism can comprise a control mechanism that can adapt to an external high-speed motor-driven handpiece via a flexible bearing shaft (or drive cable) that drives the inner cutting member of the operable tip.

A second actuation mechanism can comprise a bending control mechanism which comprises a trigger, ring, or one or more actuating buttons on the handle. The handle can be hollow and house apparatus that connects the actuation mechanism to the flexible distal end segment. The apparatus that connects the bending control mechanism to the flexible distal end segment can include one or more tensioning members such as cables or push/pull rods or metal ribbons in connection with a bending cam that causes the flexible distal end segment to bend upon rotation of the bending cam.

A third control mechanism can provide the means to rotate the outer cutting window member of the operable tip independent of the flexible distal end segment. It can be rotatable about the arcuate axis of the non-rotating outer distal end segment.

The present invention can articulate in any combination of the following five degrees of freedom, which are described in more detail herein: (i) translation along the axis of the tubular outer body member, resulting from the surgeon inserting or withdrawing the device from the body, (ii) curvilinear bending of a distal portion of the surgical instrument, (iii) rotation about the linear axis of the outer tube resulting from the surgeon rotating his/her wrist and hand, (iv) rotation of the outer cutting window member of the operable tip relative to the outer tube, and (v) rotation of the inner cutting member of the operable tip relative to the outer cutting window member.

The operable tip can be removable and interchangeable. The inner cutting member can be removable and interchangeable. The operable tip may comprise a powered blade with suction, and the device can further comprise an actuation mechanism disposed at its proximal end. This actuation mechanism may comprise a flexible actuating cable that can be connected to an external drive motor. Thus, tissue and other material can be pulled into the operable tip using suction and the tissue and other material can be resected and withdrawn through the device using the inner cutting member in combination with suction (e.g., by connecting the surgical instrument to a vacuum source).

The entire surgical instrument, or one or more portions of the surgical instrument, such as the inner member, elongate member, and/or operable end, can be disposable.

The entire device, or one or more parts of the device, can be reusable.

In another aspect of the present invention, the invention generally relates to a medical device kit, comprising one or more of the components set forth herein. The one or more surgical instruments can be packaged in sterile condition.

In another aspect of the present invention, the invention generally relates to a method for performing minimally invasive diagnostic and surgical procedures on the hip, the method comprising:

(a) providing an operable surgical instrument comprising a handle disposed at the proximal end; an operable tip disposed at the distal end; a rigid outer tube extending between the handle and the operable tip; a flexible distal end segment; an outer cutting window member of the operable tip being rotatably connected relative to the flexible distal end segment; a flexible actuating cable to drive a high-speed inner cutting member of the operable tip; the handle comprising control means to maneuver the operable tip by iteratively adjusting one or more of the following degrees of freedom: linear translation of the operable end into the hip joint capsule, resulting from the surgeon inserting or withdrawing the instrument from the body; rotation of the surgical instrument about the linear axis of the outer tube by rotating the handle with a twisting motion of the wrist; curvilinear bending of the flexible distal end segment; rotation of the outer window cutting member about an arcuate axis of a bend in the flexible distal end segment; and high-speed rotation of the inner cutting member;

(b) configuring the flexible distal end segment into a straight configuration;

(c) inserting the distal end of the surgical instrument into the body and into the hip capsule;

(d) iteratively adjusting the curvilinear bend radius of the flexible distal end segment while translating the operable tip toward the operative target;

(e) rotating the outer cutting window member to face the surgical target;

(f) actuating the high speed inner cutting member;

(g) performing the procedure;

(h) configuring the flexible distal end segment into a straight configuration; and (i) removing the surgical instrument from the capsule.

In one preferred form of the present invention, there is provided a surgical instrument, said surgical instrument comprising:

a hollow shaft having a distal end and a proximal end;

a handle disposed at said proximal end of said hollow shaft;

a flexible distal end segment disposed at said distal end of said hollow shaft, said flexible distal end segment comprising a distal end and a proximal end, with said proximal end of said flexible distal end segment being mounted to said distal end of said hollow shaft;

at least one tensioning member extending between said distal end of said flexible distal end segment and said handle for manipulating said distal end of said flexible distal end segment relative to said hollow shaft whereby to provide curvilinear bending of said flexible distal end segment relative to said hollow shaft;

an outer cutting window member rotatably mounted to said distal end of said flexible distal end segment;

an inner extension tube extending through said hollow shaft and said flexible distal end segment for selectively rotating said outer cutting window member relative to said flexible distal end segment, said inner extension tube having a distal end and a proximal end, said distal end of said inner extension tube being mounted to said outer cutting window member and said proximal end of said inner extension tube extending to said handle;

an inner cutting member rotatably disposed within said outer cutting window member; and a rotational element for rotating said inner cutting member relative to said outer cutting window member, said rotational element comprising a distal end connected to said inner cutting member and a proximal end extending to said handle;

wherein said surgical instrument is configured so as to provide at least the following independent degrees of freedom: curvilinear bending of said flexible distal end segment relative to said flexible distal end segment, rotation of said outer cutting window member relative to said flexible distal end segment, and rotation of said inner cutting member relative to said outer cutting window member.

In another preferred form of the present invention, there is provided a method for performing a procedure, said method comprising:

providing a surgical instrument, said surgical instrument comprising:

a hollow shaft having a distal end and a proximal end;

a handle disposed at said proximal end of said hollow shaft;

a flexible distal end segment disposed at said distal end of said hollow shaft, said flexible distal end segment comprising a distal end and a proximal end, with said proximal end of said flexible distal end segment being mounted to said distal end of said hollow shaft;

at least one tensioning member extending between said distal end of said flexible distal end segment and said handle for manipulating said distal end of said flexible distal end segment relative to said hollow shaft whereby to provide curvilinear bending of said flexible distal end segment relative to said hollow shaft;

an outer cutting window member rotatably mounted to said distal end of said flexible distal end segment;

an inner extension tube extending through said hollow shaft and said flexible distal end segment for selectively rotating said outer cutting window member relative to said flexible distal end segment, said inner extension tube having a distal end and a proximal end, said distal end of said inner extension tube being mounted to said outer cutting window member and said proximal end of said inner extension tube extending to said handle;

an inner cutting member rotatably disposed within said outer cutting window member; and a rotational element for rotating said inner cutting member relative to said outer cutting window member, said rotational element comprising a distal end connected to said inner cutting member and a proximal end extending to said handle;

wherein said surgical instrument is configured so as to provide at least the following independent degrees of freedom: curvilinear bending of said flexible distal end segment relative to said flexible distal end segment, rotation of said outer cutting window member relative to said flexible distal end segment, and rotation of said inner cutting member relative to said outer cutting window member;

manipulating said handle so as to advance said outer cutting window member at a selected site; and performing at least one of curvilinear bending of said flexible distal end segment relative to said flexible distal end segment, rotation of said outer cutting window member relative to said flexible distal end segment, and rotation of said inner cutting member relative to said outer cutting window member.

In another preferred form of the present invention, there is provided a surgical instrument, said surgical instrument comprising:

a hollow shaft having a distal end and a proximal end;

a handle disposed at said proximal end of said hollow shaft;

a flexible distal end segment disposed at said distal end of said hollow shaft, said flexible distal end segment comprising a distal end and a proximal end, with said proximal end of said flexible distal end segment being mounted to said distal end of said hollow shaft;

at least one tensioning member extending between said distal end of said flexible distal end segment and said handle for manipulating said distal end of said flexible distal end segment relative to said hollow shaft whereby to provide curvilinear bending of said flexible distal end segment relative to said hollow shaft;

an outer cutting window member rotatably mounted to said distal end of said flexible distal end segment;

an inner extension tube extending through said hollow shaft and said flexible distal end segment for selectively rotating said outer cutting window member relative to said flexible distal end segment, said inner extension tube having a distal end and a proximal end, said distal end of said inner extension tube being mounted to said outer cutting window member and said proximal end of said inner extension tube extending to said handle;

at least one spring for yieldably biasing said inner extension tube proximally so as to yieldably bias said outer cutting window member proximally against said distal end of said flexible distal end segment;

an inner cutting member rotatably disposed within said outer cutting window member; and a rotational element for rotating said inner cutting member relative to said outer cutting window member, said rotational element comprising a distal end connected to said inner cutting member and a proximal end extending to said handle;

wherein said surgical instrument is configured so as to provide at least the following independent degrees of freedom: curvilinear bending of said flexible distal end segment relative to said flexible distal end segment, rotation of said outer cutting window member relative to said flexible distal end segment, and rotation of said inner cutting member relative to said outer cutting window member.

BRIEF DESCRIPTION OF THE DRAWINGS

The foregoing and other objects, features and advantages of the present invention, as well as the invention itself, will be more fully understood from the following detailed description of the preferred embodiments, which is to be read together with the accompanying drawings, in which:

FIGS. 8A and 8B are schematic views showing how the inner extension tube may be spring biased proximally so as to keep the outer cutting window member biased against the flexible distal end segment;

DETAILED DESCRIPTION OF THE PREFERRED EMBODIMENTS

Figure 1:
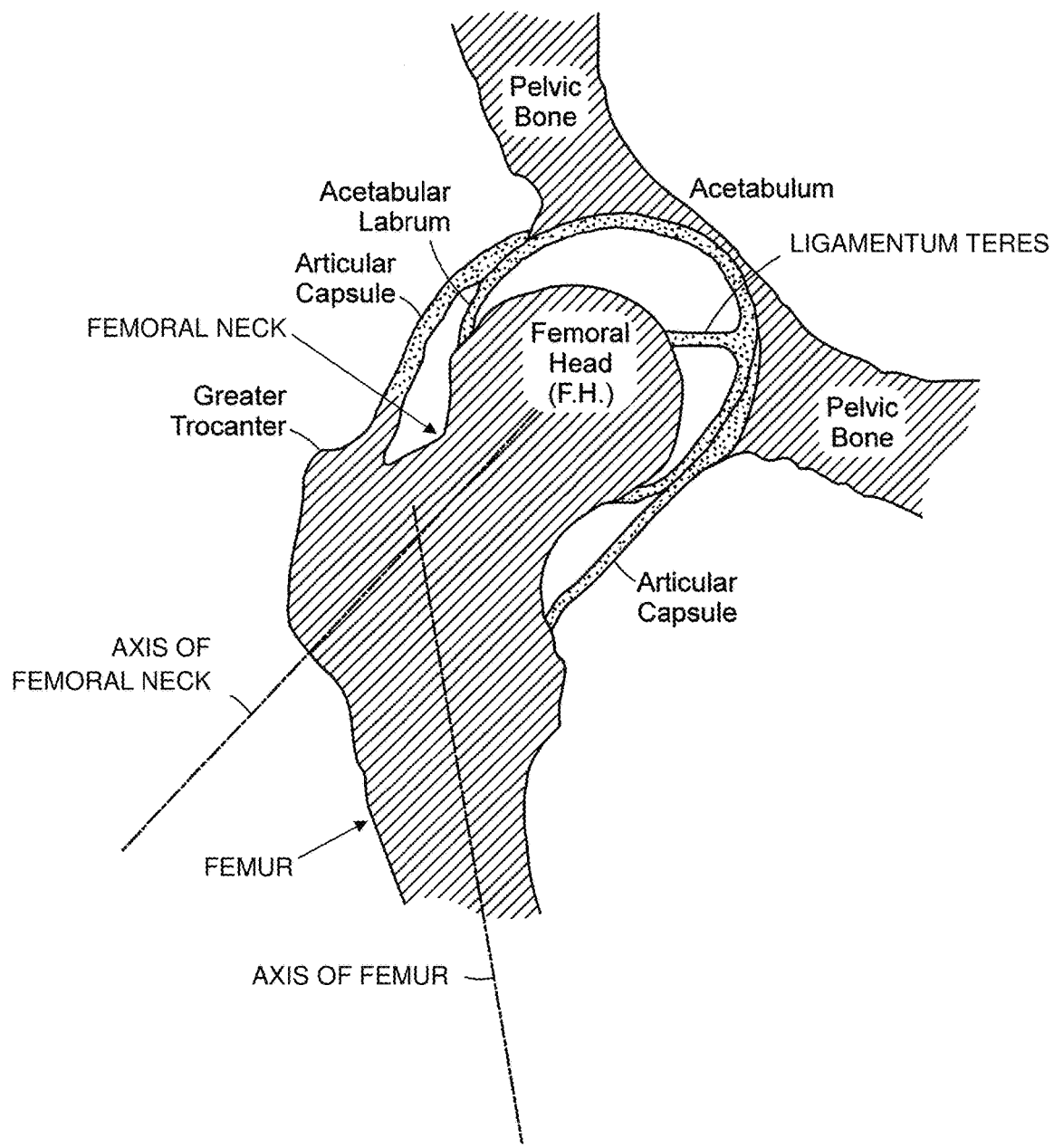
FIG. 1 is a schematic view showing a cross-sectional anterior view of a distended right hip joint.
Figure 2A:
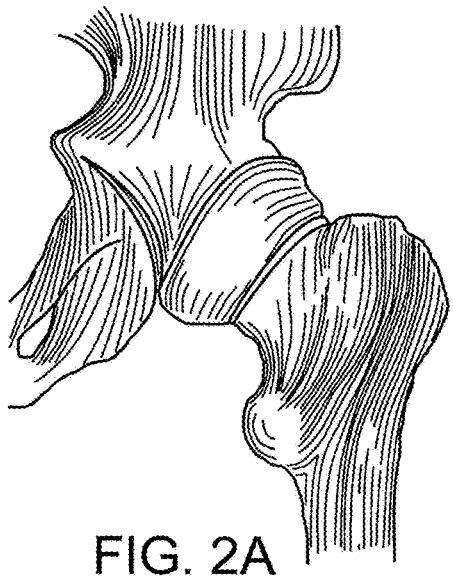
FIG. 2A is a schematic view showing a posterior view of the right hip joint.
Figure 2B:
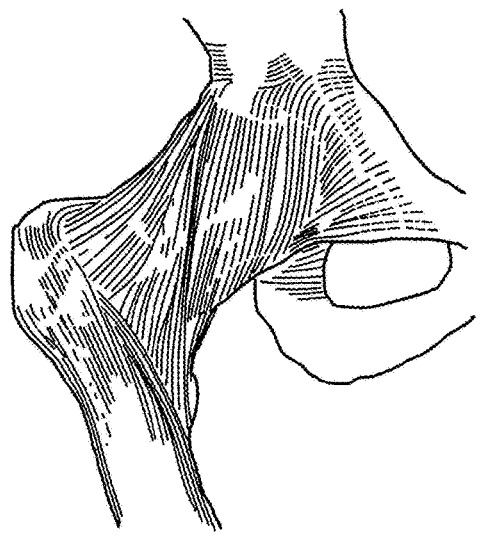
FIG. 2B is a schematic view showing an anterior view of a right hip joint with various ligaments shown.
Figure 2C:
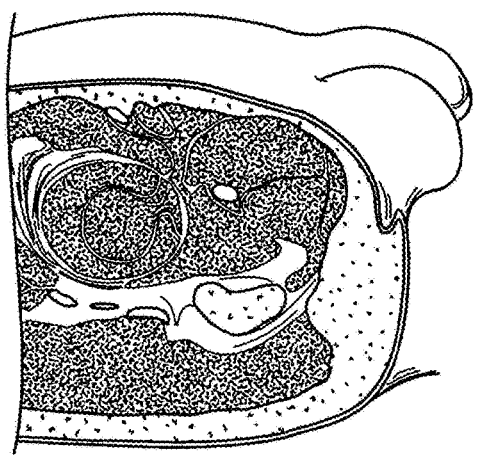
FIG. 2C is a schematic view showing the anatomical structures surrounding the right hip joint.
Figure 2D:
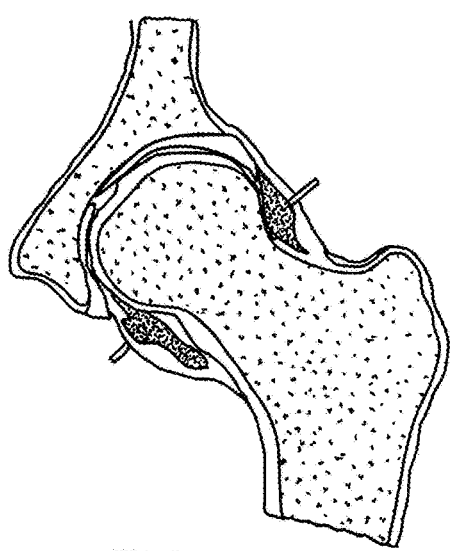
FIG. 2D is a schematic view showing a cross-sectional posterior view of the right hip joint.
Figure 3:
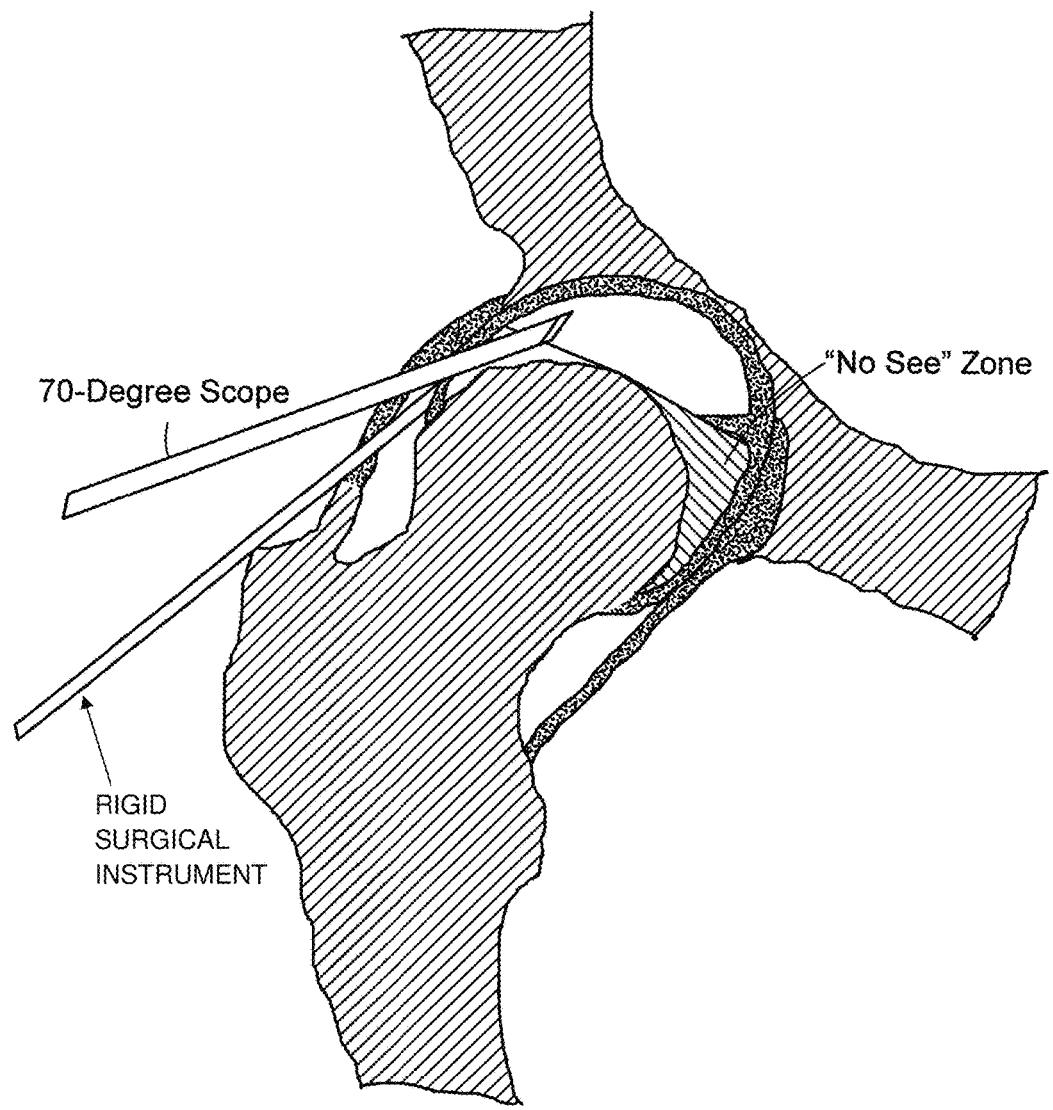
FIG. 3 is a schematic view showing access to the hip joint using a "70 degree" arthroscope and a rigid surgical instrument.
Figure 4:
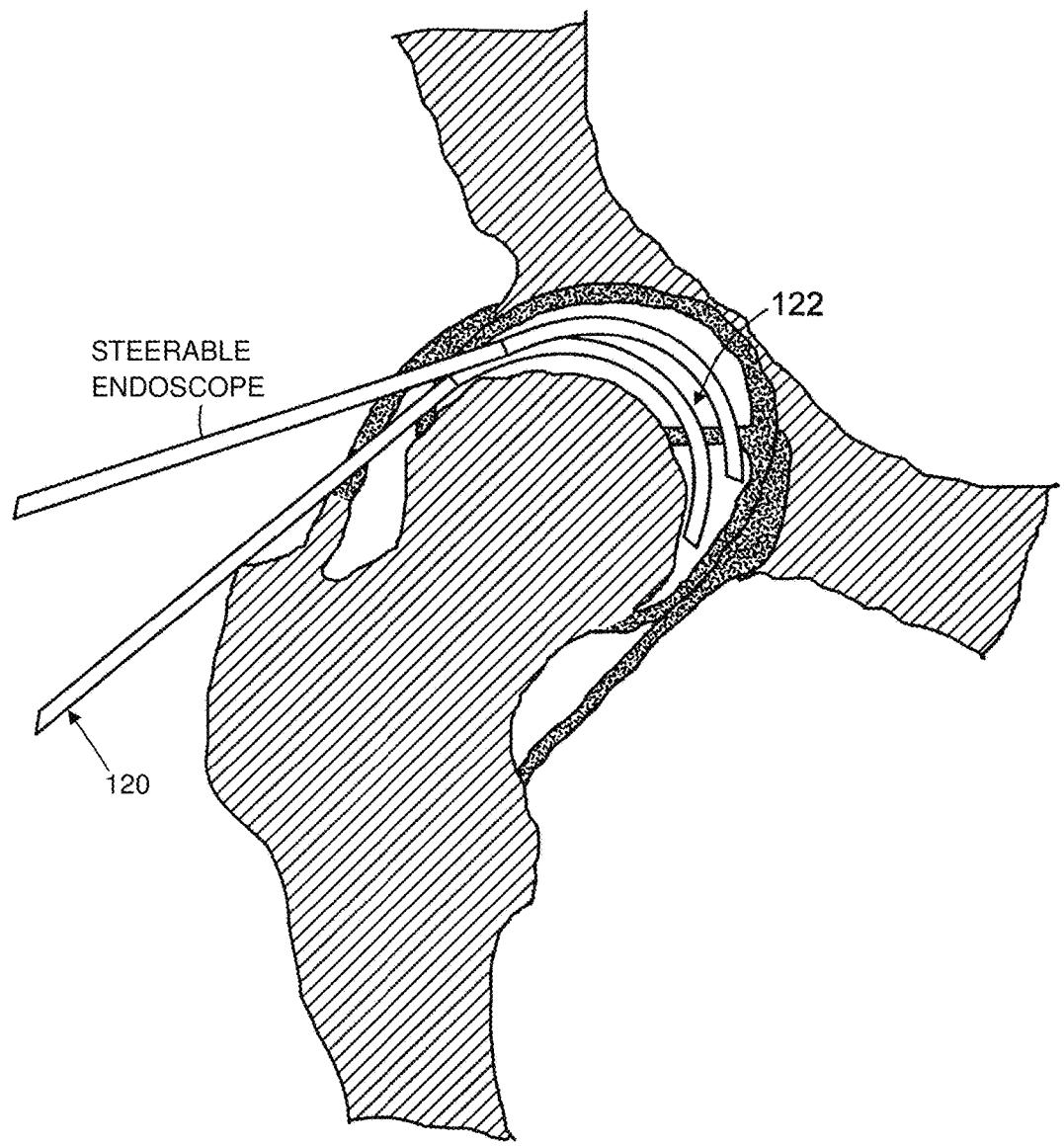
FIG. 4 is a schematic view showing access to the hip joint in accordance with the present invention (i.e., using a steerable arthroscope and a steerable surgical instrument)
Figure 5:
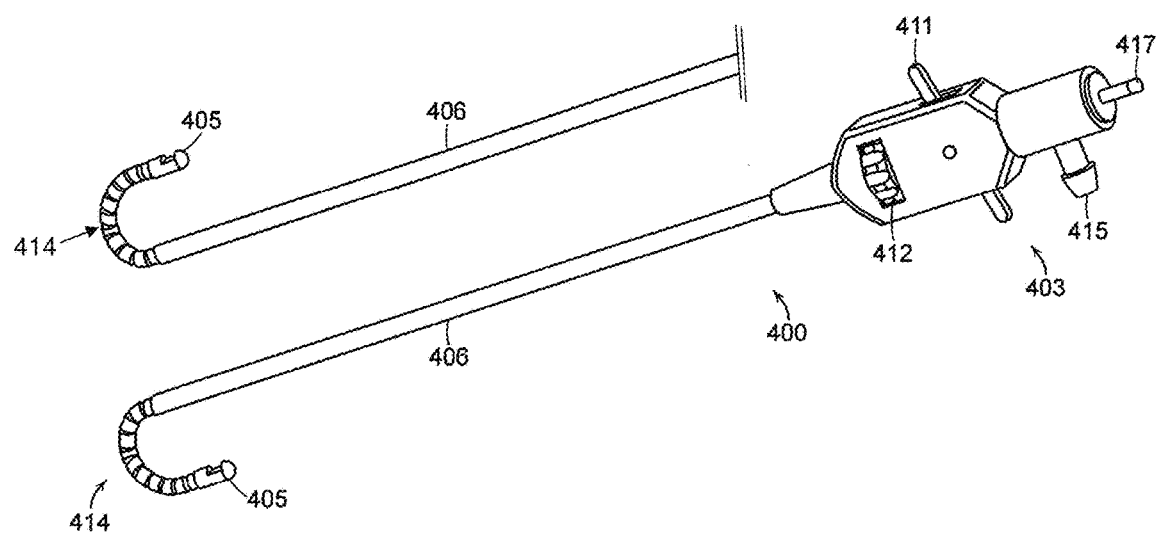
FIG. 5 is a schematic view showing a novel surgical instrument formed in accordance with the present invention.

The methods and apparatus of the present invention are primarily illustrated and described herein by means of surgical instruments which have been adapted for use in performing arthroscopic procedures on the hip. The methods and apparatus described herein provide access to the internal portions of the distended hip capsule during arthroscopic procedures that are presently not accessible using currently available arthroscopic instruments. The methods and apparatus of the present invention can suitably be used to perform arthroscopic procedures not only on the hip, but also on other parts of the body, such as the knee and shoulder. The surgical instruments are particularly suitable for performing procedures on parts of the body that require flexible access. The methods and apparatus of the present invention are not limited to arthroscopy, and can further be used in endoscopic and laparoscopic procedures as well as open surgeries. The surgical instruments of the present invention can be in the general form of any conventional surgical instrument including, but not limited to, a tubular tissue-cutting device wherein the cutting element is disposed within an outer window element and can be rotated by means of a motor. Thus, the disclosure to follow should be construed in an illustrative sense rather than in a limiting sense.

First Embodiment

In a first embodiment, with reference to FIGS. 5-10, an operable tip 405 is independently rotatable relative to a flexible distal end segment 414 which is fixed to the distal end of an outer tube 406. Operable end 405 comprises an outer cutting window member 423 (FIG. 6A) comprising a cutting window 423A and an inner cutting member 424 which together provide a tissue cutting function when inner cutting member 424 is rotated relative to cutting window 423A. A handle 403 (FIG. 5) houses the actuation means for controlling (i) the bending of flexible distal end segment 414 relative to outer tube 406 (and hence the disposition of operable end 405 relative to handle 403), (ii) the rotation of outer cutting window member 423 relative to flexible distal end segment 414 (and hence the disposition of cutting window 423A relative to handle 403), and (iii) high-speed driver features which control rotation of inner cutting member 424 relative to flexible distal end segment 414 (and hence the rotation of inner cutting member 424 relative to outer cutting window member 423).

Figure 6A:
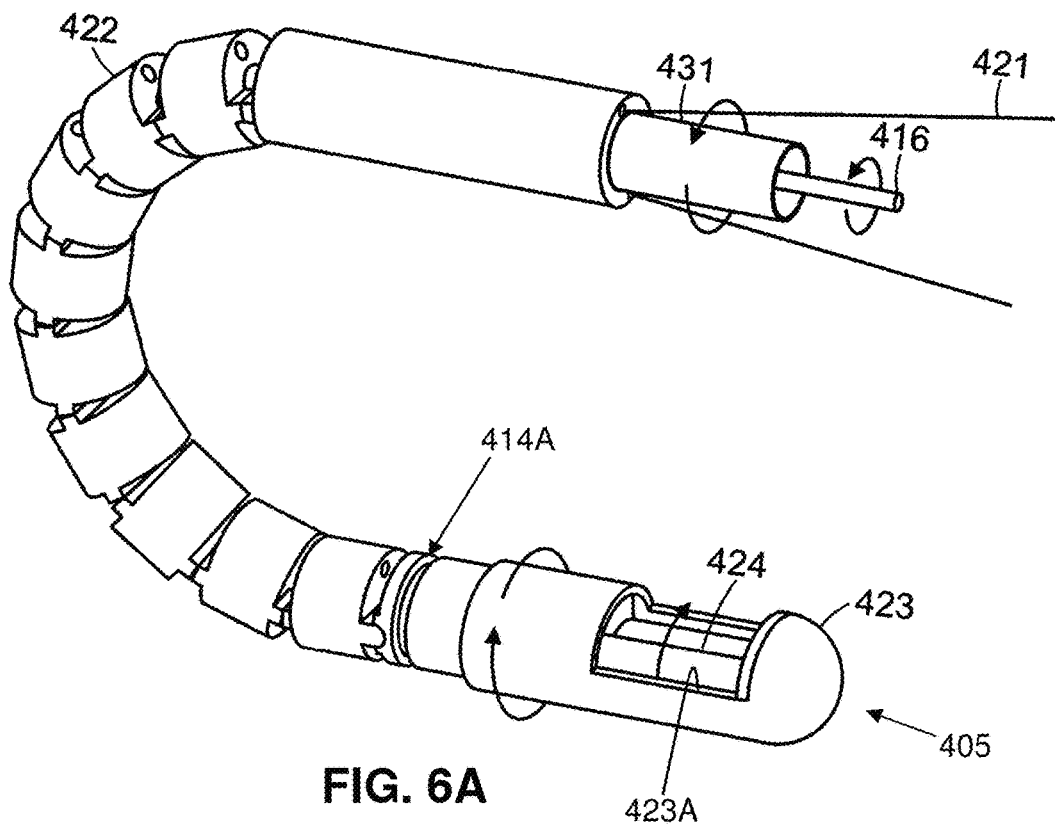
FIGS. 6A, 6B and 6C are schematic views showing various configurations of the distal end of the novel surgical instrument shown in FIG. 5.
Figure 6B:
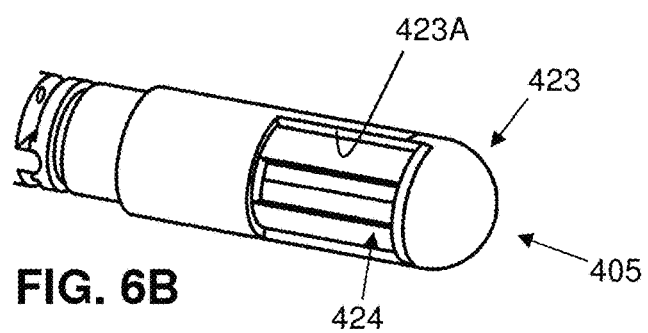
Figure 6C:
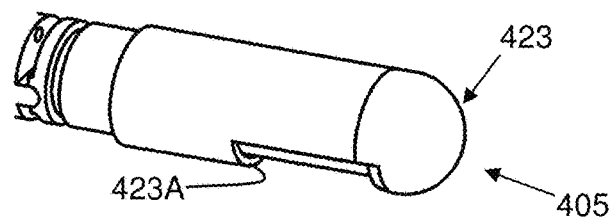
Figure 7A:
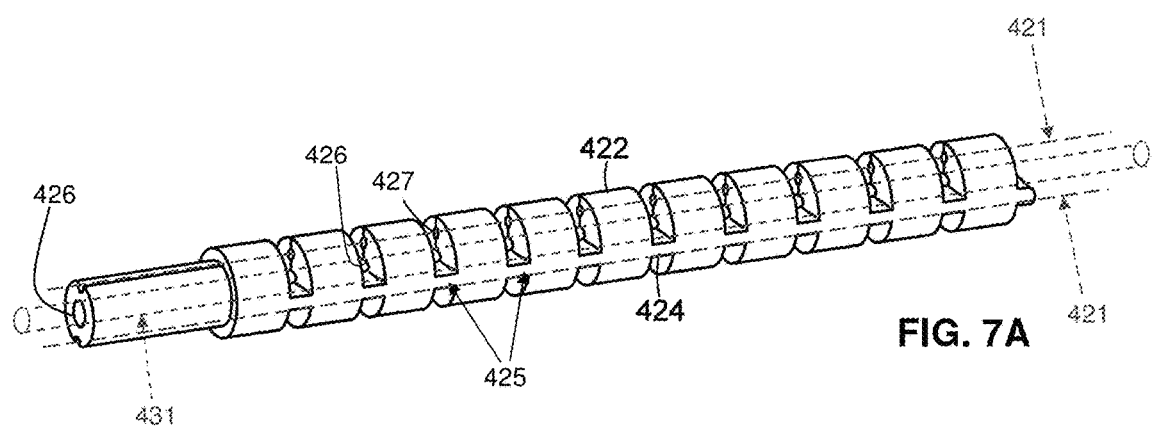
FIGS. 7A and 7B are schematic views showing a one-piece molded flexible distal end segment which is utilized in the distal end of the novel surgical instrument shown in FIG. 5.
Figure 7B:
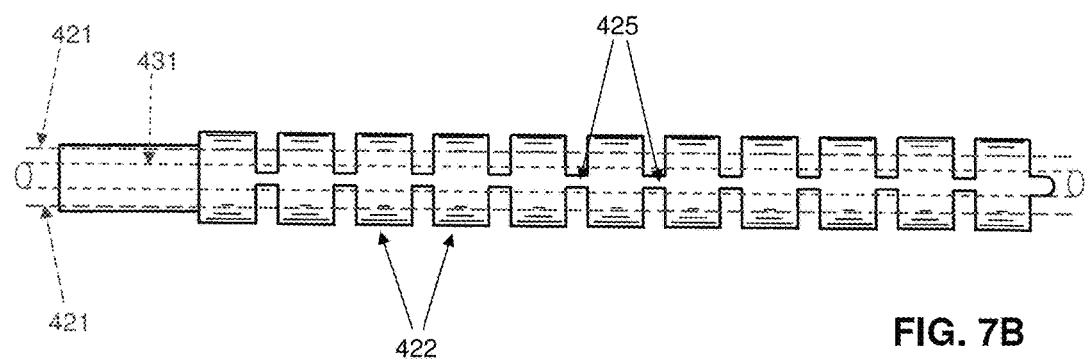

(i) The bending of flexible distal end segment 414 relative to outer tube 406 is achieved by the actuation of two diametrically-opposed tensioning members 421 (FIG. 8), which are connected to bending cam 411 in handle 403 and extend through outer tube 406 and flexible distal end segment 414, with tensioning members 421 being attached to the distal end of flexible distal end segment 414 (FIG. 6A). As bending cam 411 is pivoted within handle 403, it places one or the other of the tensioning members 421 in tension which, in turn, bends flexible distal end segment 414 in one direction.

Figure 8:
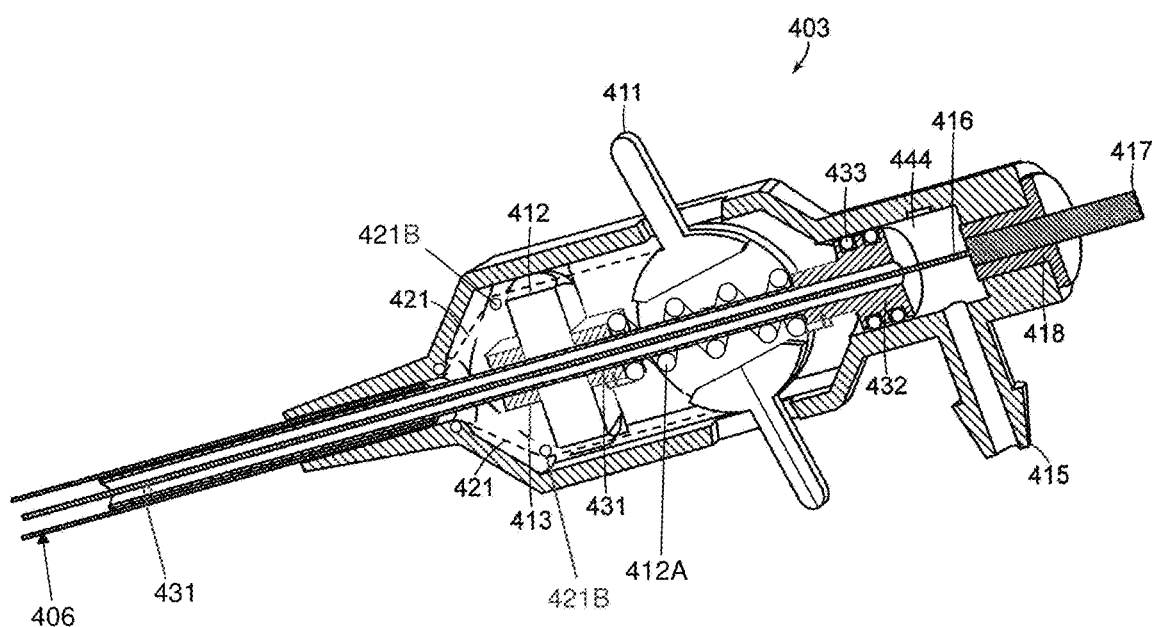
FIG. 8 is a schematic view showing the handle of a first embodiment of the novel surgical instrument shown in FIG. 5.
Figure 9:
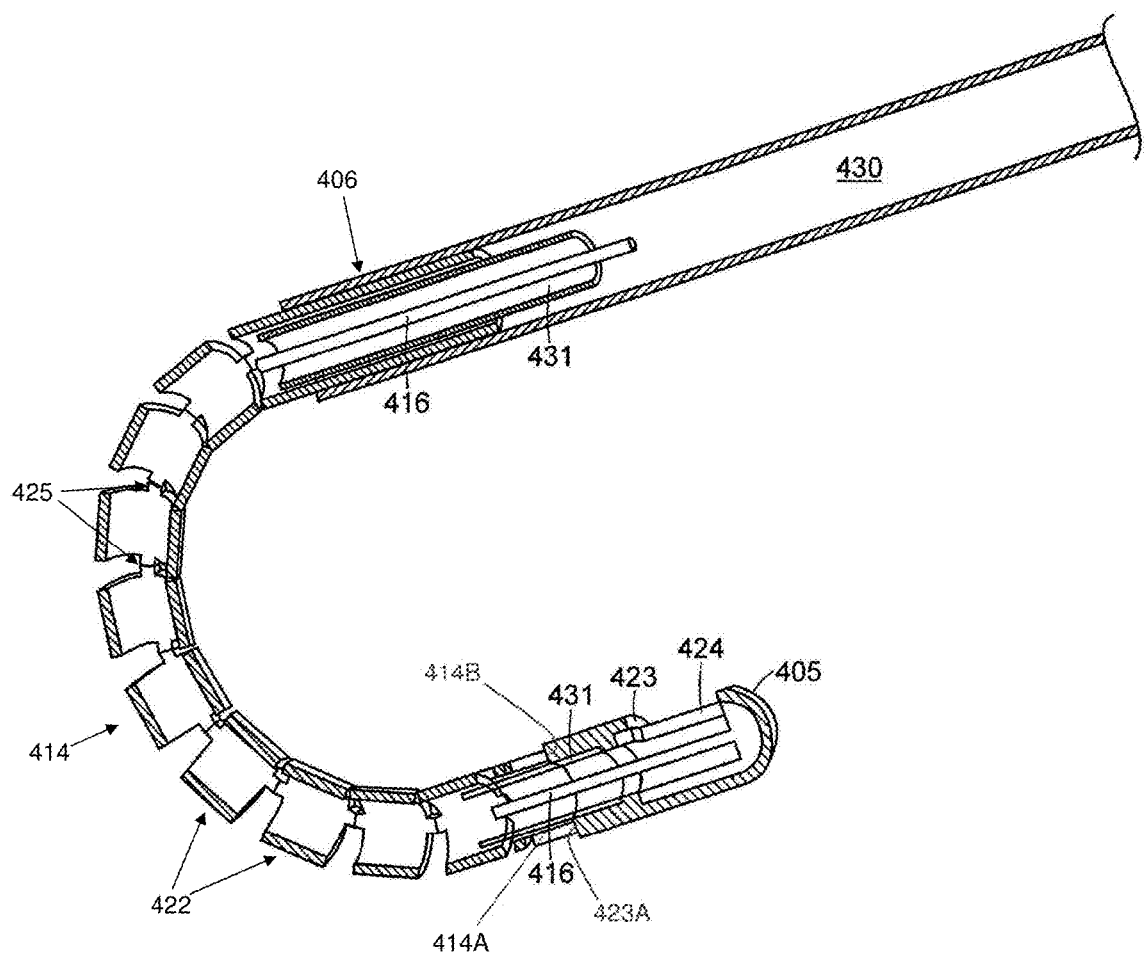
FIG. 9 is a schematic view showing the distal end of the first embodiment of the novel surgical instrument which uses the handle shown in FIG. 8.

(ii) The rotation of outer cutting window member 423 of operable tip 405 is controlled by the rotation of a rotation control knob 412 (FIG. 5) which is connected to an inner extension tube 431 (FIGS. 6A and 8) which extends through outer tube 406 and flexible distal end segment 414 and is secured to outer cutting window member 423 of operable tip 405 (FIG. 9). This rotation positions cutting window 423A in a desired rotational position relative to handle 403, e.g., for improved tissue access. Note the difference in window position in the three views shown in FIGS. 6A, 6B and 6C as rotation control knob 412 turns outer cutting window member 423 (and hence turns cutting window 423A). In a first position shown in FIG. 6A, cutting window 423A is positioned on the inside of the bend arc of flexible distal end segment 414; in a second position shown in FIG. 6B, cutting window 423A is positioned on the side of the bend arc of flexible distal end segment 414; and in a third position shown in FIG. 6C, cutting window 423A is positioned on the outside of the bend arc of flexible distal end segment 414.

(iii) The actuation of operable tip 405 (i.e., the rotation of inner cutting member 424 relative to flexible distal end segment 414, and hence the rotation of inner cutting member 424 relative to outer cutting window member 423) is controlled by rotation of a bearing shaft 417 (FIG. 5) and a flexible actuating cable 416 (FIGS. 6A and 8), with flexible actuating cable 416 being secured at its distal end to inner cutting member 424 (FIG. 9). Bearing shaft 417 is designed to interface with an external drive motor (not shown). This actuation of bearing shaft 417 turns actuating cable 416 which turns inner cutting member 424 within operable tip 405 (i.e., within outer cutting window member 423). Resected tissue from operable tip 405 is removed from the joint by applying suction (from an external suction source) to a suction hose fitting 415. Inner cutting member 424 of operable tip 405 can have different cutting characteristics for different surgical requirements. For example, the cutting of soft tissue generally requires that inner cutting member 424 comprise a sharp edge, e.g., as shown FIGS. 6A, 6B and 6C. Bone, however, is generally resected using a burr that uses many small sharp ridges to grind the bone surface rather than attempting to slice it with a sharp edge, e.g., such as a burr 605 shown in FIGS. 10A, 10B and 10C.

As discussed above, handle 403 houses the various means for controlling operation of the distal end of the surgical instrument, i.e., the bending of flexible distal end segment 414 relative to the longitudinal axis of outer tube 406, the rotation of outer cutting window member 423 of operable tip 405 relative to flexible distal end segment 414, and the high-speed rotation of inner cutting member 424 relative to outer cutting window member 423. Tension steering means (i.e., bending cam 411 and tensioning members 421) are provided for controlling the bend radius of flexible distal end segment 414. Tensioning members 421 are selected to meet the requirements for stiffness and flexibility of flexible distal end segment 414. Woven or braided cables generally provide the best flexibility, and flat ribbons of stainless steel or Nitinol generally provide the best stiffness. Other materials and/or cross-sectional configurations are available for applications that present other unique requirements. Tensioning members 421 terminate distally on the most distal end of flexible distal end segment 414 (FIG. 6A) and are controlled by bending cam 411 located in handle 403. As seen in FIG. 9, a circumferential groove 414A is provided in the distal-most vertebra 422 to contain a circumferential wrap of tensioning members 421.

Flexible distal end segment 414 can be in the form of a single-piece, injection-molded plastic part (FIGS. 7A and 7B), made from materials chosen for the their bending fatigue resistance properties as well as their lubricious bearing properties, e.g., urethane, nylon, PEEK, Teflon and the like. The configuration of flexible distal end segment 414 preferably comprises a series of vertebra 422 interconnected by beam-shaped webs 425. As the tension in one of tensioning members 421 is increased, the vertebrae 422 surrounding that tensioning member move closer together, thereby placing the beam-shaped webs 425 in a state of bending. Webs 424 bend like a beam rather than a pivot. The stress is distributed linearly over the distance between the neutral axis and the thickness of the beam. This improves the fatigue life of the beam-shaped webs 424, by avoiding the stress riser point loads that are common with a pivotally-hinged geometry as opposed to a bending geometry. Flexible distal end segment 414 can further comprise at least one axial hole 426 through which inner extension tube 431 (FIG. 6A) can pass (for the purpose of rotating outer cutting window member 423), as well as holes or slots 427 (shown in the 12 o'clock and 6 o'clock positions) for receiving tensioning members 421.

Tensioning members 421 are routed around strategically-positioned bearings 421B and connected to bending cam 411 (FIG. 8) which can be conveniently positioned for rotation by the thumb or forefinger. As bending cam 411 is rotated, one of the pair of tensioning members 421 is placed into tension so as to bend flexible distal end segment 414 in proportion to the tension that is applied. The other tensioning member 421 is slackened so as to extend over its elongated distance.

Rotation control knob 412 (FIGS. 5 and 8) can be rotated (e.g., in bearing saddles 413, FIG. 8) and can be conveniently disposed for rotation by a finger (e.g., the forefinger) or the thumb. Inner extension tube 431 (FIG. 6A) is secured to rotation control knob 412, such that when rotation control knob 412 is rotated, inner extension tube 431 rotates as well, however, rotation control knob 412 is preferably biased proximally (e.g., under the pulling force applied by a preload spring 412A) so as to bias inner extension tube 431 proximally. The distal end of inner extension tube 431 is connected to the proximal end of outer cutting window member 423 (FIG. 9) of operable tip 405. The proximal end of inner extension tube 431 can terminate in a housing 432 (FIG. 8) which is sealed to the interior of handle 403 with seals 433 (e.g., O-ring seals). Seals 433 are provided to hold the vacuum in a vacuum chamber 444 while still permitting rotation of inner extension tube 431 and housing 432. Vacuum chamber 444 is connected with an external vacuum source via suction hose fitting 415. As noted above, the proximal end of flexible actuating cable 416 (FIGS. 6A and 8) is connected to bearing shaft 417. Bearing shaft 417 rotates in a shaft seal 418 (FIG. 8) which maintains the vacuum of vacuum chamber 444. Vacuum chamber 444 pulls fluid and resected tissue from operable tip 405, through inner extension tube 431 and out of the surgical instrument through suction hose fitting 415. To prevent tissue from clogging the interior of inner extension tube 431, flexible actuating cable 416 can be designed and disposed to rotate in a random, non-linear pattern so as to disrupt any tissue aggregation. This random, non-linear pattern can be kept irregular by varying the rotational speed of actuating cable 416. In this respect it will be appreciated that it is well known by those skilled in the art that a high-speed driven cable seeks equilibrium by deflecting its shaft into a sinusoidal shape, the amplitude and period of which changes by changing the speed of rotation or by changing the distance between the supporting bearings at each end of the cable. By way of example but not limitation, flexible actuating cable 416 can rotate within the limits of "straight on the center line" with low speed or in contact with the walls of inner extension tube 431 with high speed. During bending of flexible distal end segment 414, the geometry of the bend is such that the outer cutting window member 423 extends slightly beyond the distal end of flexible distal end segment 414 (as it compresses during bending) which can compromise the lateral bearing strength of operable tip 405. To compensate for this, the rotation control knob 412 can be configured to (i) allow the inner extension tube 431 to translate axially in response to the pulling force applied by spring 412A, and (ii) rotationally secure the inner extension tube 431 to rotation control knob 412 by means well known in the art (e.g., by engaging a hex-shaped feature, not shown, mounted to the outer diameter of inner extension tube 431).

Thus, in one preferred form of the invention, and looking now at FIG. 8, rotation control knob 412 is spring biased proximally by spring 412A so as to spring bias inner extension tube 431 proximally, and hence to spring bias outer cutting window member 423 into contact with the distal end of flexible distal end segment 414.

Alternatively, other means may be provided for spring biasing inner extension tube 431 proximally so as to pull outer cutting window member 423 proximally against the distal end of flexible distal end segment 414.

By way of example but not limitation, and looking now at FIGS. 8, 8A and 8B, inner extension tube 431 is sized and positioned so that when flexible distal end segment 414 is bent, inner extension tube 431 is also bent and conforms to the arc established by the inner passage of flexible distal end segment 414. This, in turn, will cause the flexible actuating cable 416 to bend, as flexible actuating cable 416 also conforms to the inner passage of inner extension tube 431. Inner extension tube 431 is further configured so that when it is bent, its distal end engages surface 423A of outer cutting window member 423 (FIGS. 8A and 8B) and its proximal end engages rotation control knob 412 (see FIG. 8).

Inner extension tube 431 is further configured so that when the flexible distal end segment 414 is in a straight, unbent configuration, the side wall of inner extension tube 431 is in a relaxed state.

In one preferred form of the invention, at least the distal end of inner extension tube 431 may comprise coils, and when flexible distal end segment 414 is in a straight, unbent configuration, the coils which comprise inner extension tube 431 are in a relaxed state in which there is no space between the adjacent coils. As best seen in FIG. 8B, inner extension tube 431 is also configured so that when it is bent, a radially inward (with respect to the arc established by the bend) portion of each coil of inner extension tube 431 remains in contact with a radially inward portion of each adjacent coil. At the same time, a space is introduced between a radially outward portion of each coil of inner extension tube 431 and a radially outward portion of each adjacent coil. In a particular embodiment, the coils of inner extension tube 431 are substantially rectangular as illustrated in FIGS. 8A and 8B.

Tensioning members 421 may be used to bend flexible distal end segment 414 so as to allow flexible distal end segment 414 to take on a desired curvature. The size and configuration of vertebrae 422 of flexible distal end segment 414 provide structure so that flexible distal end segment 414 may be selectively curved with relatively little force on the tensioning members 421. The slidably disposed inner extension tube 431 is forced by vertebrae 422 to adopt a conforming curvature.

As discussed above, in order to prevent the protrusion of inner extension tube 431 from the distal end of flexible distal end segment 414 during bending of flexible distal end segment 414, the spring 412A may be provided in handle 403 for biasing inner extension tube 431 proximally. Alternatively, and/or additionally, a spring 412B (FIGS. 8A and 8B) may be provided within outer tube 406, near the distal end of outer tube 406, whereby to bias inner extension tube 431 proximally relative to outer tube 406 (and hence bias inner extension tube 431 proximally relative to flexible distal end segment 414). By virtue of this construction, spring 412B biases inner extension tube 431 (and hence outer cutting window member 423) proximally so as to ensure that when the flexible distal end segment 414 is bent, outer cutting window member 423 remains in contact with the distal end of the flexible distal end segment 414. As a result of the biasing force provided by spring 412A (and/or by spring 412B), the proximal end of inner extension tube 431 is forced to move in the proximal direction such that the "excess length" of inner extension tube 431 (which occurs when flexible distal end segment 414 is bent) is drawn into outer tube 406.

As shown in FIGS. 8A and 8B, spring 412B is preferably disposed circumferentially around inner extension tube 431 within the interior of outer tube 406. Outer tube 406 is preferably formed with an inwardly extending tab 434 (or other stopping mechanism) that engages the distal end of spring 412B, and inner extension tube 431 is preferably formed with an outwardly extending circumferential flange 435 (or other stopping structure) for engaging the proximal end of the spring 412B. As shown in FIG. 8A, when flexible distal end segment 414 is in an uncurved configuration, the spring 412B is in a relatively compressed state. As shown in FIG. 8B, when flexible distal end segment 414 is curved, the effective length of inner extension tube 431 is greater than the effective length of flexible distal end segment 414. However, the biasing force of spring 412B acting on inner extension tube 431 keeps outer cutting window member 423 in contact with the flexible distal end segment 414 and causes the inner extension tube 431 to be withdrawn in the proximal direction.

It will be understood that the biasing mechanisms discussed above (i.e., springs 412A and/or 412B) are not limited to use in conjunction with the vertebrate flexible members of the illustrated embodiment, but could be used in conjunction with any elongate surgical instrument embodiment of the invention that has a curvable end segment with two coaxially disposed flexible members having different lengths when the curvable end segment is curved.

Figure 10A:
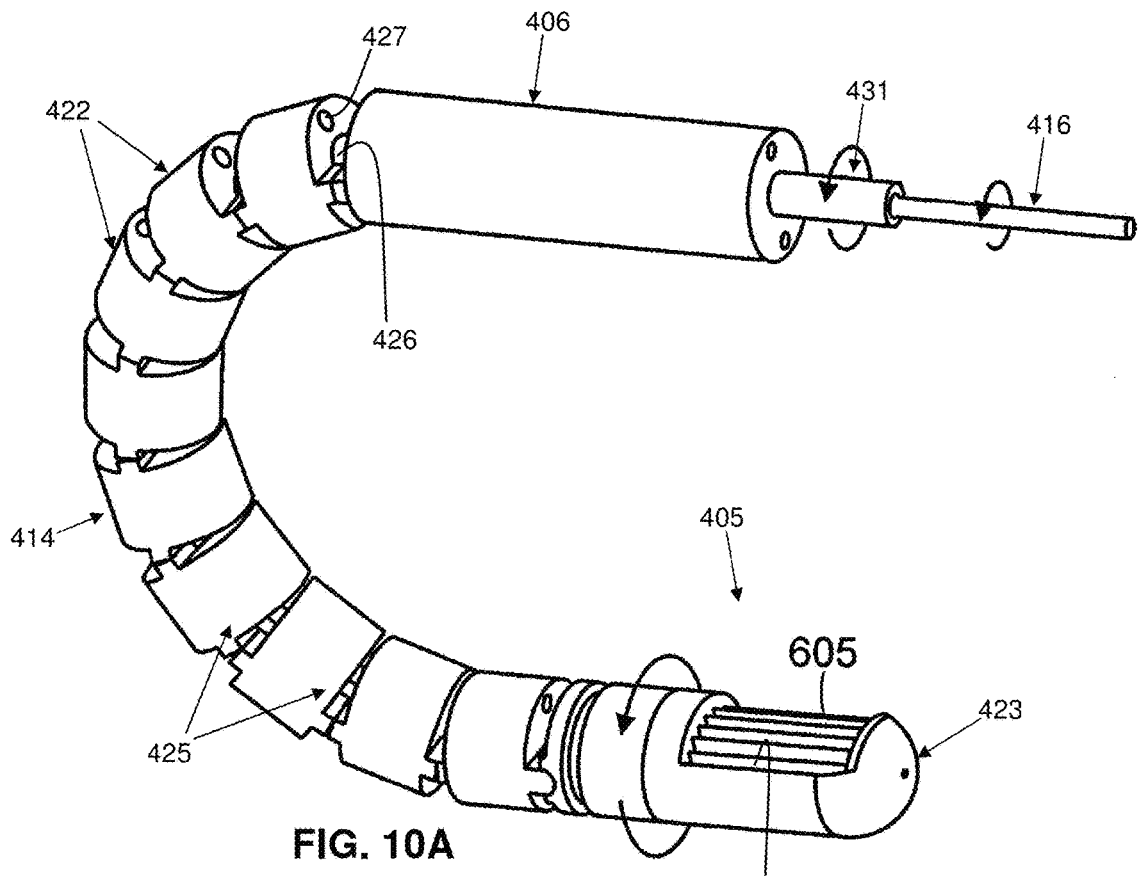
FIGS. 10A, 10B and 10C are schematic views similar to the views of FIGS. 6A, 6B and 6C, showing the distal end of the novel surgical instrument comprising a burr.
Figure 10B:
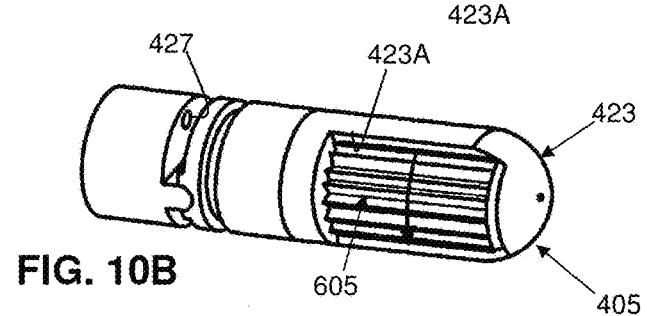
Figure 10C:
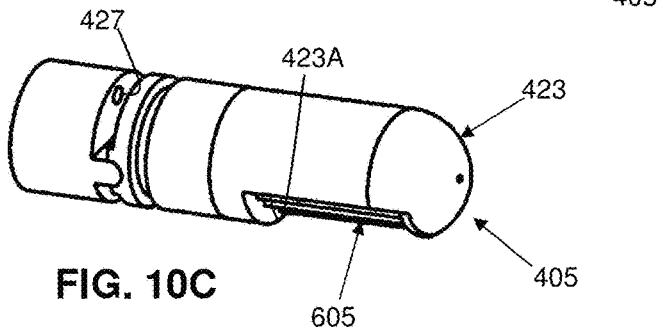

Flexible actuating cable 416 is secured at its distal end to inner cutting member 424 of operable tip 405 as shown in FIG. 9. Inner cutting member 424 rotates freely within outer cutting window member 423. Tissue is resected as it is drawn into cutting window 423A and is engaged by inner cutting member 424. By way of example but not limitation, where inner cutting member 424 comprises a windowed structure having cutting edges, tissue is excised as the cutting edges of inner cutting member 424 sweep across cutting window 423A (FIGS. 6A, 6B, 6C and 9). By way of further example but not limitation, where inner cutting member 424 comprises a burr, tissue is excised as tissue is engaged by the burr (FIGS. 10A, 10B and 10C). Inner extension tube 431 is designed to form a close sliding fit with flexible distal end segment 414, such that flexible distal end segment 414 serves as a rotational bearing surface for inner extension tube 431, and the material comprising flexible end segment 414 is selected for the required bearing friction characteristics. The most distal face of flexible distal end segment 414 (i.e., the portion 414A of flexible distal end segment 414 that is in contact with surface 423A of outer cutting window member 423) is also a thrust bearing surface.

Thus it will be seen that in accordance with the present invention, there is provided a novel steerable surgical instrument 5 which generally comprises an outer tube 406, a flexible distal end segment 414 secured to the distal end of outer tube 406, and a handle 403 secured to the proximal end of outer tube 406. Flexible distal end segment 414 comprises a flexible structure formed from a plurality of vertebra 422 interconnected by beam-shaped webs 425.

Tensioning members 421 extend between bending cam 411 in handle 403 and the distal end of flexible distal end segment 414, such that bending cam 411 controls bending of the distal tip of flexible distal end segment 414. Tensioning members 421 extend through holes 427 in vertebrae 422 in flexible distal end segment 414.

Outer cutting window member 423 is movably mounted to the distal end of flexible distal end segment 414. Inner extension tube 431 extends between rotation control knob 412 in handle 403 and outer cutting window member 423, such that rotation control knob 412 controls the rotational disposition of outer cutting window member 423 (and hence the rotational disposition of cutting window 423A). Inner extension tube 431 extends through axial hole 426 in vertebrae 422 in flexible distal end segment 414.

Inner cutting member 424 is movably disposed within outer cutting window member 423. Flexible actuating cable 416 extends between bearing shaft 417 (which is attachable to a drive motor) and inner cutting member 424, such that rotation of bearing shaft 417 causes rotation of inner cutting member 424 within outer cutting window member 423, whereby to cut tissue. Flexible actuating cable 416 extends through inner extension tube 431.

Thus it will be seen that (i) bending cam 411 in handle 403 controls bending of flexible distal end segment 414 (and hence the bending disposition of operable tip 405 relative to handle 403), (ii) rotation control knob 412 in handle 403 controls the rotational disposition of outer cutting window member 423 (and hence the rotational disposition of cutting window 423A relative to handle 403), and (iii) rotation of bearing shaft 417 controls rotation of inner cutting member 424 (and hence cutting action at cutting window 423A).

Suction hose fitting 415 allows suction to be applied to the interior of novel steerable surgical instrument 5, such that tissue cut by operable tip 405 can be removed from the surgical site.

Second Embodiment

Figure 11:
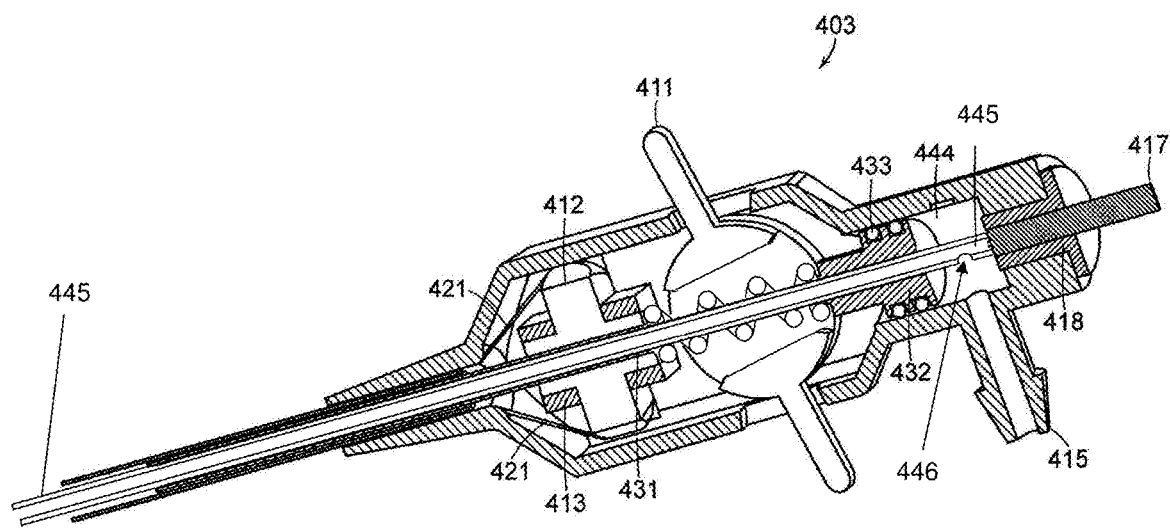
FIG. 11 is a schematic view showing the handle of a second embodiment of the novel surgical instrument shown in FIG. 5.
Figure 12:
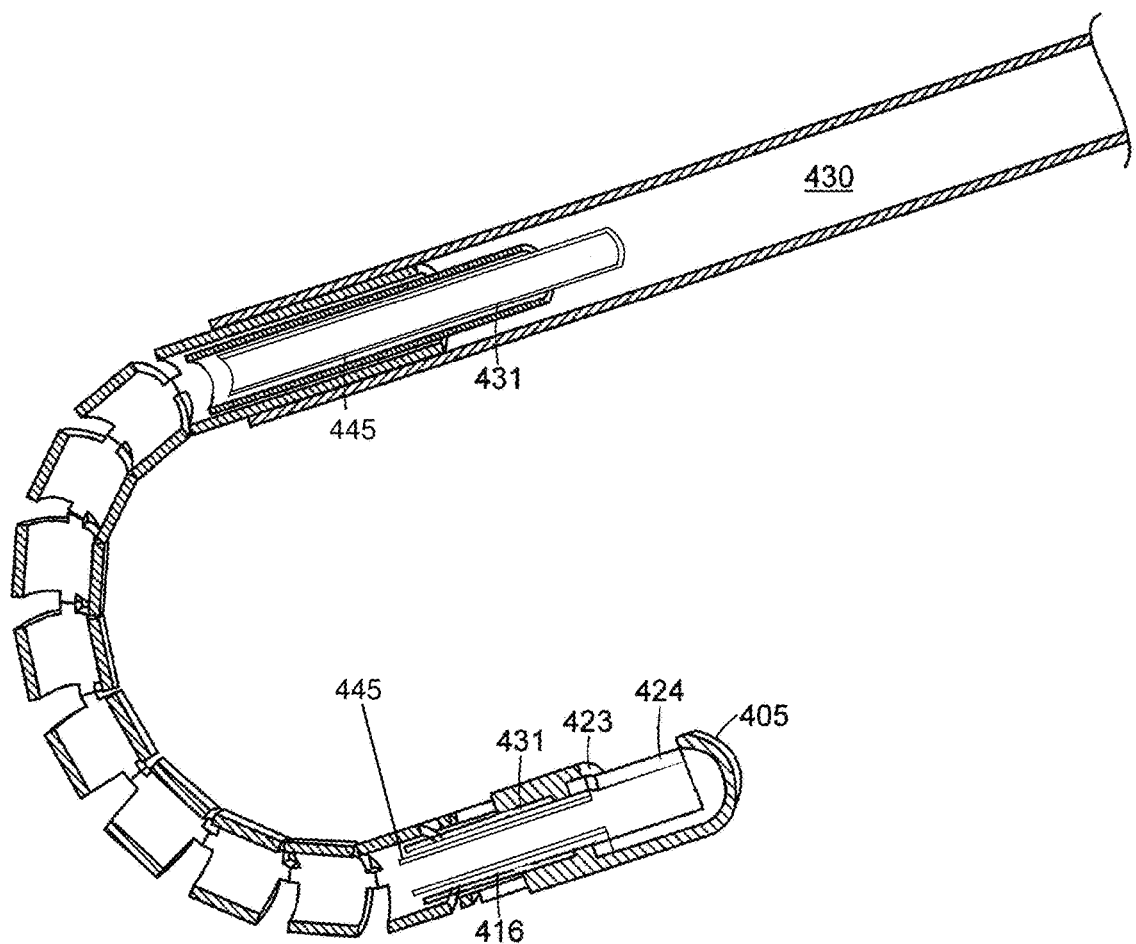
FIG. 12 is a schematic view showing the distal end of the second embodiment of the novel surgical instrument which uses the handle shown in FIG. 11.

In a second embodiment of the present invention, and looking now at FIGS. 11 and 12, flexible actuating cable 416 is replaced by a high-speed inner extension tube 445 that is secured at its distal end to inner cutting member 424 and is secured at its proximal end to bearing shaft 417. High-speed inner extension tube 445 provides a rotating window 446 which is open to vacuum chamber 444. As a result, tissue resected into inner cutting member 424 is withdrawn by vacuum into vacuum chamber 444 via the lumen of high speed inner extension tube 445, where it is evacuated via suction hose fitting 415. Note that in this form of the invention, sealed housing 432 is preferably joined with bearing shaft 417 such that sealed housing 432 and bearing shaft 417 serve as rotating seals to preserve the vacuum in vacuum chamber 444.

Third Embodiment

Figure 13:
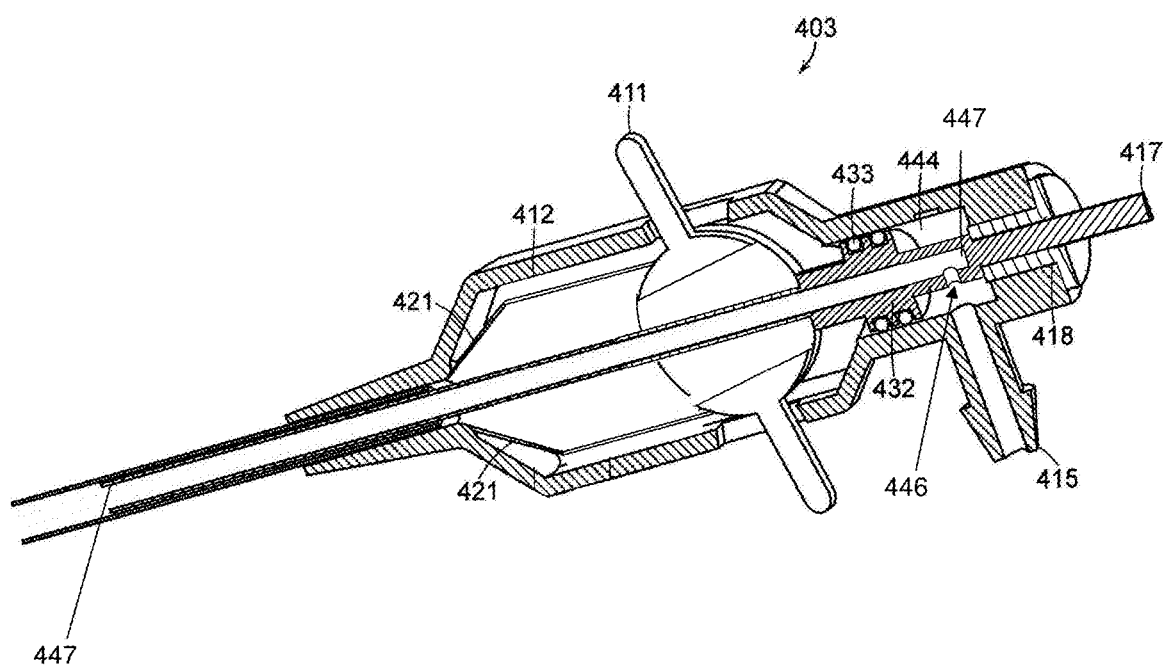
FIG. 13 is a schematic view showing the handle of a third embodiment of the novel surgical instrument shown in FIG. 5.
Figure 14:
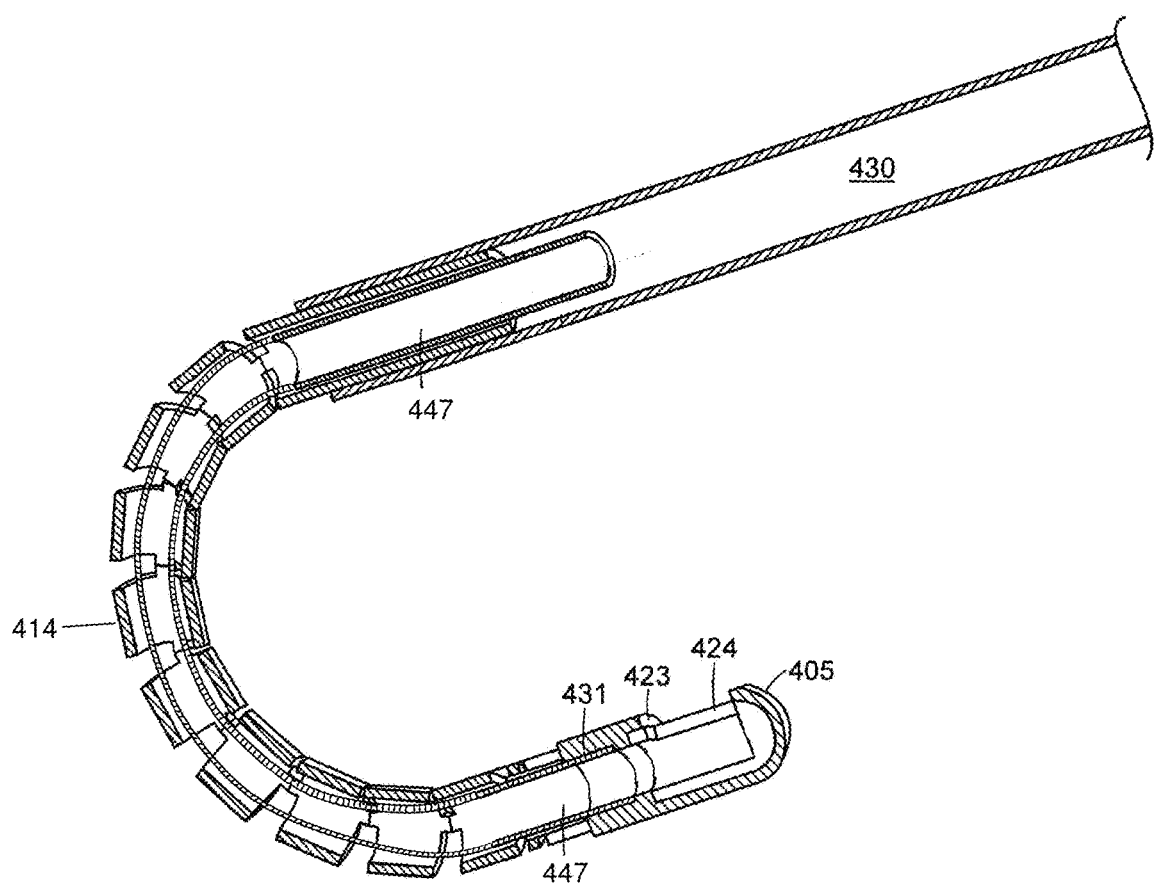
FIG. 14 is a schematic view showing the distal end of the third embodiment of the novel surgical instrument which uses the handle shown in FIG. 13.
Figure 14A:
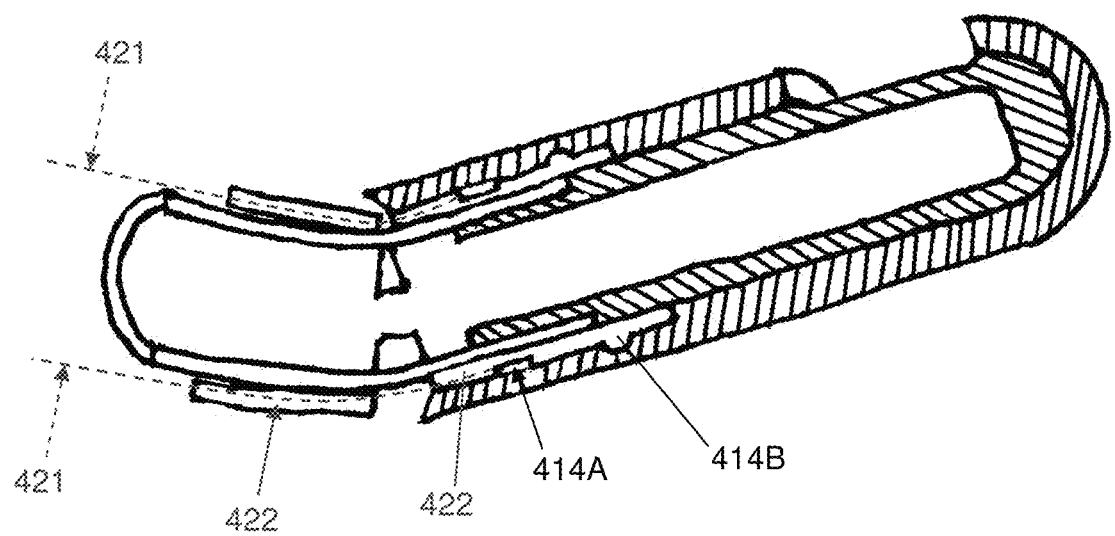
FIGS. 14A and 14B are schematic views showing constructions for the distal end of the novel surgical instrument shown in FIGS. 13 and 14.
Figure 14B:
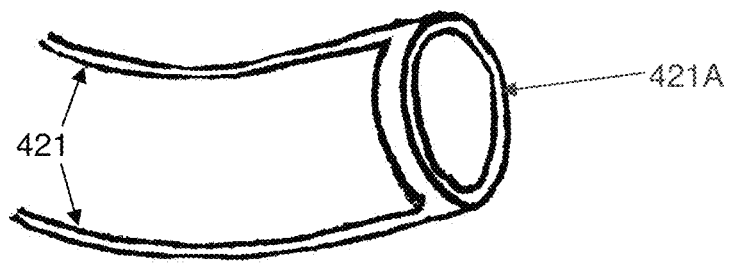

In a third embodiment of the present invention, and looking now at FIGS. 13 and 14, the aforementioned rotation control knob 412 is omitted. More particularly, in this form of the invention, outer cutting window member 423 is rotationally connected to flexible distal end segment 414 in a manner that allows the surgeon to rotate outer cutting window member 423 by hand before inserting the distal end of the surgical instrument into the joint. It is secured axially via molded retaining ring 414B (FIG. 14A). The last-set position of outer cutting window member 423 remains static throughout the surgical procedure (or until the surgeon chooses to withdraw the distal end of the surgical instrument from the joint and reposition outer cutting window member 423). To accommodate the snap-fit feature of the outer cutting window member 423 to the molded retaining ring feature 414B, the tensioning member 421 is fashioned as a flat ring 421A as shown in FIG. 14B such that the flat ring is secured in the circumferential molded recess 414A in the most distal vertebra. With this embodiment of the present invention, the aforementioned inner extension tube 431 is replaced by inner tubular drive shaft 447 which has its distal end connected to inner cutting member 424 instead of to outer cutting window member 423 (as is the case with the aforementioned first and second embodiments). In this form of the invention, inner tubular drive shaft 447 serves to rotate inner cutting member 424 of operable tip 405. The proximal end of inner tubular drive shaft 447 is joined to sealed housing 432 which is, in turn, fixed to bearing shaft 417. Thus, turning bearing shaft 417 (e.g., with a drive motor) turns sealed housing 432, which turns inner extension tube 447, which turns inner cutting member 424. A vacuum window 446 is provided in both inner tubular drive shaft 447 and sealed housing 432 for providing fluid communication between operable tip 405 and vacuum chamber 444.

ADDITIONAL ASPECTS OF THE INVENTION

For each of the embodiments of the present invention, some or all of the surgical instrument can be reusable. Alternatively some or all of the surgical instrument can be disposable. In some embodiments of the present invention, removable and/or interchangeable distal ends, inner/outer body member(s), and/or elongate body members can be provided that are reusable or disposable, as desired.

The present invention also comprises methods for performing arthroscopic procedures using the embodiments discussed above so as to access the entire joint, with or without switching cannulated access portals. These methods are performed using embodiments of the present invention that flexibly move within the surgical field by bending flexible distal end segment 414, rotating outer cutting window member 423 of operable tip 405, and rotating inner cutting member 424. Thus, it will be appreciated that the present invention is capable of accessing the entire distended capsule volume of the joint and eliminating any "No See" zones within the surgical field. The present invention may also obviate the need for inserting the surgical instrument into more than one access portal in order to allow for the access of the entire joint.

In another embodiment of the present invention, the invention generally relates to a method for performing minimally-invasive hip arthroscopic surgical procedures by providing a surgical instrument comprising a handle at the proximal end, a flexible or curvable portion at the distal end, and an elongate body member extending therebetween. An operable tip is rotatably mounted at the distal end. The bend radius of the flexible or curvable portion can be controlled with at least one bending tensioning member (e.g., at least one flexible cable) in the flexible distal end segment, and can be tensioned by rotation of a cam-like actuator located in the handle so as to achieve the desired bend radius. In each instance, the user can iteratively adjust the degree of bending to accurately position the operable tip in the joint. The method of the present invention further comprises (i) positioning the flexible (or curvable) distal portion into a straight configuration by tensioning a system of opposing tensioning members until the flexible (or curvable) distal end segment is straight; (ii) inserting the straight elongate member into the hip capsule; (iii) iteratively adjusting the bend radius to position the operable tip in the desired arcuate position through the manipulation of control mechanisms in the handle; (iv) iteratively adjusting the degree of rotation about the linear axis of the elongated body member; (v) adjusting the rotational position of the outer cutting window member of the operable tip about its arcuate axis to the desired rotational orientation using control mechanisms in the handle; (vi) performing the intended procedure by rotating the inner cutting member of the operable tip (e.g., by connecting the inner cutting element to an external, hand-held motorized device); (vii) re-establishing the straight configuration of the flexible distal end segment; and (viii) removing the device from the body.

Methods in accordance with the foregoing aspects of the present invention can further comprise multiple surgical instruments. By way of example but not limitation, after the visualization portal has been established, it may be necessary to use one surgical instrument to resect tissue (e.g., a punch), a second surgical instrument to remove tissue and loose bodies, a third surgical instrument to cauterize any remaining bleeding sites, etc.

The present invention also comprises kits (not shown) that comprise one or more surgical instruments formed in accordance with the present invention and packaged in sterile condition. Such kits also may include one or more interchangeable operable tips, rigid and flexible tubular interconnecting body members for use with the portions of the surgical instrument that may be reusable. In some embodiments, the kit includes flexible and/or rigid access cannulas that are sealed against the saline distension pressure established within the joint capsule and inserted using "safe access" trocars, mechanical flexation device(s) that mechanically distend the hip joint laterally as well as longitudinally along the line of action coincident with the center line of the femoral neck, and fluid management systems to control the flow and pressure of the saline in the hip capsule.

The foregoing description of the invention is intended to be merely illustrative thereof, and it will be appreciated that variations and modifications can be effected without departing from the scope or spirit of the invention as set forth in the following claims. By way of example but not limitation, the bend-and-rotate approach for the precise delivery of a multiplicity of operable tips provides significant utility beyond the hip applications described herein, (e.g., knee and shoulder arthroscopy, as well as smaller joint arthroscopy). The smaller diameter of the surgical instrument, as well as the flexibility of the surgical instrument, also makes it useful for other applications that require delicate tissue manipulation including, but not limited to, laparoscopic cholecystectomies, appendectomies, hernia repair, bariatric gastric bypass, and certain thoracic and spinal procedures.

What is claimed is:

1. A surgical instrument, said surgical instrument comprising:
   a hollow shaft having a distal end and a proximal end;
   a handle disposed at said proximal end of said hollow shaft;
   a flexible distal end segment disposed at said distal end of said hollow shaft, said flexible distal end segment comprising a distal end and a proximal end, with said proximal end of said flexible distal end segment being mounted to said distal end of said hollow shaft;
   at least one tensioning member extending between said distal end of said flexible distal end segment and said handle for manipulating said distal end of said flexible distal end segment relative to said hollow shaft whereby to provide curvilinear bending of said flexible distal end segment relative to said hollow shaft;
   an outer cutting window member rotatably mounted to said distal end of said flexible distal end segment;
   an inner extension tube extending through said hollow shaft and said flexible distal end segment for selectively rotating said outer cutting window member relative to said flexible distal end segment, said inner extension tube having a distal end and a proximal end, said distal end of said inner extension tube being mounted to said outer cutting window member and said proximal end of said inner extension tube extending to said handle;
   an inner cutting member rotatably disposed within said outer cutting window member; and
   a rotational element for rotating said inner cutting member relative to said outer cutting window member, said rotational element comprising a distal end connected to said inner cutting member and a proximal end extending to said handle;
   wherein:
   said surgical instrument provides at least the following independent degrees of freedom: curvilinear bending of said flexible distal end segment relative to said flexible distal end segment, rotation of said outer cutting window member relative to said flexible distal end segment, and rotation of said inner cutting member relative to said outer cutting window member; and
   said independent degrees of freedom occur relative to a stationary position of said hollow shaft.

2. A surgical instrument according to claim 1 wherein said flexible distal end segment comprises a plurality of vertebrae which are interconnected with one another by at least one web.

3. A surgical instrument according to claim 2 wherein said at least one web deflects in the manner of a beam when subjected to bending forces.

4. A surgical instrument according to claim 2 wherein said plurality of vertebrae are interconnected with one another by two webs of the at least one web.

5. A surgical instrument according to claim 4 wherein said two webs are diametrically opposed from one another.

6. A surgical instrument according to claim 2 wherein said flexible distal end segment comprises a single, integral piece.

7. A surgical instrument according to claim 1 wherein said flexible distal end segment comprises at least one opening extending therethrough, and further wherein said at least one tensioning member extends through said at least one opening.

8. A surgical instrument according to claim 1 wherein said flexible distal end segment comprises at least one passageway extending therethrough, and further wherein said inner extension tube extends through said at least one passageway.

9. A surgical instrument according to claim 1 wherein said at least one tensioning member comprises two tensioning members.

10. A surgical instrument according to claim 9 wherein said two tensioning members each comprise a distal end and a proximal end, and further wherein said distal ends of said two tensioning members are secured to said distal end of said flexible distal end segment and said proximal ends of said two tensioning members extend to said handle.

11. A surgical instrument according to claim 9 wherein said two tensioning members are diametrically opposed from one another as they extend along said flexible distal end segment and said hollow shaft.

12. A surgical instrument according to claim 9 further comprising a bending cam mounted to said handle for selectively applying tension to said two tensioning members, and further wherein said proximal ends of said two tensioning members are secured to said bending cam.

13. A surgical instrument according to claim 1 further comprising a rotation control knob movably mounted to said handle, said proximal end of said inner extension tube being mounted to said rotation control knob.

14. A surgical instrument according to claim 13 wherein said rotational element comprises a flexible actuating cable.

15. A surgical instrument, said surgical instrument comprising:
   a hollow shaft having a distal end and a proximal end;
   a handle disposed at said proximal end of said hollow shaft;
   a flexible distal end segment disposed at said distal end of said hollow shaft, said flexible distal end segment comprising a distal end and a proximal end, with said proximal end of said flexible distal end segment being mounted to said distal end of said hollow shaft;
   at least one tensioning member extending between said distal end of said flexible distal end segment and said handle for manipulating said distal end of said flexible distal end segment relative to said hollow shaft whereby to provide curvilinear bending of said flexible distal end segment relative to said hollow shaft;
   an outer cutting window member rotatably mounted to said distal end of said flexible distal end segment;
   an inner extension tube extending through said hollow shaft and said flexible distal end segment for selectively rotating said outer cutting window member relative to said flexible distal end segment, said inner extension tube having a distal end and a proximal end, said distal end of said inner extension tube being mounted to said outer cutting window member and said proximal end of said inner extension tube extending to said handle;
   at least one spring for yieldably biasing said inner extension tube proximally so as to yieldably bias said outer cutting window member proximally against said distal end of said flexible distal end segment;
   an inner cutting member rotatably disposed within said outer cutting window member; and
   a rotational element for rotating said inner cutting member relative to said outer cutting window member, said rotational element comprising a distal end connected to said inner cutting member and a proximal end extending to said handle;

wherein said surgical instrument is configured so as to provide at least the following independent degrees of freedom: curvilinear bending of said flexible distal end segment relative to said flexible distal end segment and a stationary position of said hollow shaft, rotation of said outer cutting window member relative to said flexible distal end segment and said stationary position of said hollow shaft, and rotation of said inner cutting member relative to said outer cutting window member and said stationary position of said hollow shaft.

16. A surgical instrument according to claim 15 wherein said at least one spring is disposed at said proximal end of said hollow shaft.

17. A surgical instrument according to claim 16 wherein said handle comprises a rotation control knob mounted to said proximal end of said inner extension tube, wherein said rotation control knob can be used to selectively rotate said outer cutting window member relative to said flexible distal end segment, and further wherein said at least one spring is mounted to said rotation control knob so as to yieldably bias said rotation control knob proximally, whereby to yieldably bias said inner extension tube proximally, whereby to yieldably bias said outer cutting window member proximally against said distal end of said flexible distal end segment.

18. A surgical instrument according to claim 15 wherein said at least one spring is disposed at said distal end of said hollow shaft.

19. A surgical instrument according to claim 18 wherein said hollow shaft comprises an inner flange, said inner extension tube comprises an outer flange, and further wherein said at least one spring is disposed between said inner flange of said hollow shaft and said outer flange of said inner extension tube so as to yieldably bias said inner extension tube proximally relative to said hollow shaft, whereby to yieldably bias said outer cutting window member proximally against said distal end of said flexible distal end segment.

* * * * *